US008853375B2

(12) United States Patent
Kandimalla et al.

(10) Patent No.: US 8,853,375 B2
(45) Date of Patent: Oct. 7, 2014

(54) TOLL LIKE RECEPTOR MODULATORS

(75) Inventors: Ekambar Kandimalla, Southboro, MA (US); Lakshmi Bhagat, Framingham, MA (US); Mallikarjuna Putta, Burlington, MA (US); Daqing Wang, Bedford, MA (US); Sudhir Agrawal, Shrewsbury, MA (US)

(73) Assignee: Idera Pharmaceuticals, Inc., Cambridge, MA (US)

( * ) Notice: Subject to any disclaimer, the term of this patent is extended or adjusted under 35 U.S.C. 154(b) by 1051 days.

(21) Appl. No.: 12/192,432

(22) Filed: Aug. 15, 2008

(65) Prior Publication Data

US 2009/0053148 A1  Feb. 26, 2009

Related U.S. Application Data

(60) Provisional application No. 60/955,895, filed on Aug. 15, 2007.

(51) Int. Cl.
*C07H 21/02* (2006.01)
*C07H 21/04* (2006.01)

(52) U.S. Cl.
USPC ...................................................... 536/23.1

(58) Field of Classification Search
None
See application file for complete search history.

(56) References Cited

U.S. PATENT DOCUMENTS

| | | | |
|---|---|---|---|
| 5,912,332 | A | 6/1999 | Agrawal et al. |
| 6,426,334 | B1 | 7/2002 | Agrawal et al. |
| 7,276,489 | B2 | 10/2007 | Agrawal et al. |

FOREIGN PATENT DOCUMENTS

| | | | |
|---|---|---|---|
| WO | WO 94/01550 | * | 1/1994 |
| WO | WO2007/047396 | | 4/2007 |

OTHER PUBLICATIONS

Zhao et al (Biochemical Pharmacology vol. 51: 173-182, 1996).*
Tokunaga et al.; "Antitumor Activity of Deoxyribonucleic Acid Fraction From *Mycobacterium bovis* BCG.I. Isolation, Physicochemical Characterization, and Antitumor Activity"; J. Natl. Cancer Inst. 1984, 72:955-962.
Shimada et al.; "In Vivo Augmentation of Natural Killer Cell Activity with a Deoxyribonucleic Acid Fraction of BCG"; Jpn. H. Cancer Res., 1986, 77:808-816.
Yamamoto et la.; "In Vitro Augmentation of Natural Killer Cell Activity and Production of Interferon-α/β and -γ with Deoxyribonucleic Acid Fraction from *Mycobacterium bovis* BCG"; Jpn. J. Cancer Res., 1988 79:866-873.
Messina et al.; "Stimulation of In Vitro Murine Lymphocyte Proliferation by Bacterial DNA"; J. Immunolo., 1991, 147:1759-1764.
Zhao et al.; "Effect of Different Chemically Modified Oligodeoxynucleotides on Immune Stimulation"; Biochem. Pharmacol. 1996, 26:173-182.
Hemmi et al.; "A Toll-like receptor recognizes bacterial DNA"; Nature 2000, 408:740-745.
Zhao et al.; "Modulation of Oligonucleotide-Induced Immune Stimulation by Cyclodextrin Analogs"; Biochem Pharmacol. 1996, 52:1537-1544.
Zhao et al.; "Pattern and Kinetics of Cytokine Production Following Administration of Phosphorothioate Oligonucleotides in Mice"; Antisense Nucleic Acid Drug Dev. 1997, 7:495-502.
Zhao et al.; "Site of Chemical Modifications on CpG Containing Phosphorothioate Oligodeoxynucleotide Modulates its Immunostimulatory Activity"; Bioorg. Med. Chem. Lett. 1999, 9:3453-3458.
Zhao et al.; "Immunostimulatory Activity of CpG Containing Phosphorothioate Oligodeoxynucleotide is Modulated by Modification of a Single Deoxynucleoside"; Bioorg. Med. Chem. Lett. 2000, 10:1051-1054.
Yu et al.; "Accessible 5'-End of CpG-Containing Phosphorothioate Oligodeoxynucleotides is Essential for Immunostimulatory Activity"; Bioorg. Med. Chem. Lett. 2000, 10:2585-2588.
Yu et al.; "Modulation of Immunostimulatory Activity of CpG Oligonucleotides by Site-Specific Deletion of Nucleobases"; Bioorg. Med. Chem. Lett. 2001, 11:2263-2267.
Kandimalla et al.; "Effect of Chemical Modifications of Cytosine and Guanine in a CpG-Motif of Oligonucleotides: Structure-Immunostimulatory Activity Relationships"; Bioorg. Med. Chem. 2001, 9:807-813.
Kandimalla et al.; "Immunomodulatory Oligonucleotides Containing a Cytosine-Phosphate-2"-deoxy-7-deazaguanosine Motif as Potent Toll-Like Receptor 9 Agonists"; Proc Natl. Acad. Sci. USA, 2005, 102:6925-6930.
Kandimalla et al.; "A dinucleotide motif in oligonucleotides shows potent immunomodulatory activity and overrides species-specific recognition observed with CpG motif"; Proc Natl Acad. Sci. USA, 2003, 100:14303-14308.
Cong et al.; "Self-stabilized CpG DNAs optimally activate human B cells and plasmacytoid dendritic cells"; Biochem Biophys Res Commun. 2003, 310:1133-1139.
Kandimalla et al.; "Secondary Structures in CpG Oligonucleotides Affect Immunostimulatory Activity"; Biochem Biophys Res Commun. 2003, 306:948-953.
Kandimalla et al.; "Divergent Synthetic Nucleotide Motif Recognition Pattern: Design and Development of Potent Immunomodulatory Oligodeoxyribonucleotide Agents with Distinct Cytokine Induction Profiles"; Nucleic Acids Res. 2003, 31:2393-2400.

(Continued)

*Primary Examiner* — Richard Schnizer
(74) *Attorney, Agent, or Firm* — Wood, Phillips, Katz, Clark & Mortimer

(57) ABSTRACT

The invention relates to TLR9 antagonist compounds and their therapeutic or prophylactic use. The invention provides novel immune regulatory oligonucleotides and immunomers as antagonist of TLRs and methods of use thereof. These immune regulatory oligonucleotides have unique sequences that suppress, without completely ablating, TLR-mediated signaling in response to a TLR ligand or TLR signaling agonist. The methods may have use in the prevention and treatment of autoimmunity, inflammation, inflammatory bowel disease, lupus, allergy, asthma, infection, sepsis, cancer and immunodeficiency.

7 Claims, 7 Drawing Sheets

(56) References Cited

OTHER PUBLICATIONS

Yu et al.; "Requirement of Nucleobase Proximal to CpG Dinucleotide for Immunostimulatory Activity of Synthetic CpG DNA"; Bioorg. Med. Chem. 2003, 11:459-464.
Bhagat et al.; "CpG Penta- and Hexadeoxyribonucleotides as Potent Immunomodulatory Agents"; Biochem Biophys Res Commun. 2003, 300:853-861.
Yu et al.; "Immunomers'-Novel 3'-3'-Linked CpG Oligodeoxyribonucleotides as Potent Immunomodulatory Agents"; Nucleic Acids Res. 2002, 30:4460-4469.
Yu et al.; "Design, Synthesis, and Immunostimulatory Properties of CpG DNAs Containing Alkyl-Linker Substitutions: Role of Nucleosides in the Flanking Sequences"; J. Med. Chem. 2002, 45:4540-4548.
Yu et al.; "Potent CpG Oligonucleotides Containing Phosphodiester Linkages: In Vitro and In Vivo Immunostimulatory Properties"; Biochem Biophys Res. Commun. 2002, 297:83-90.
Kandimalla et al.; "Conjugation of Ligand at the 5"-End of CpG DNA Affects Immunostimulatory Activity"; Bioconjug. Chem. 2002, 13:966-974.
Yu et al.; "Immunostimulatory Properties of Phosphorothioate CpG DNA Containing Both 3'-5'-and 2'-5-Internucleotide Linkages"; Nucleic Acids Res. 2002, 30:1613-1619.
Yu et al.; "Immunostimulatory Activity of CpG Oligonucleotides Containing Non-Ionic Methylphosphonate Linkages"; Bioorg. Med. Chem. 2001, 9:2803-2808.
Putta et al.; "Novel Oligodeoxynucleotide Agonists of TLR9 Containing N3-Me-dC or N1-Me-dG Modifications"; Nucleic Acids Res. 2006, 34:3231-3238.
Marshak-Rothstein; "Toll-Like Receptors in Systemic Autoimmune Disease" Nat. Rev. Immunol. 2006, 6:823-835.
Papadimitraki et al.; "Toll Like Receptors and Autoimmunity: A Critical Appraisal" J. Autoimmun. 2007, 310-318.
Sun et al.; "TLR7/9 Antagonists as Therapeutics for Immune-Mediated Inflammatory Disorders"; Inflam. Allergy Drug Targets, 2007, 6:223-235.
Diebold; "Recognition of Viral Single-Stranded RNA by Toll-Like Receptors"; Adv. Drug Deliv. Rev. 2008, 60:813-823.
Cook et al.; "Toll-Like Receptors in the Pathogenesis of Human Disease"; Nature Immunol., 2004, 5:975-979.
Tse and Horner; "Defining a Role for Ambient TLR Ligand Exposures in the Genesis and Prevention of Allergic Diseases"; Semin Immunopathol. 2008, 53-62.
Tobia and Curtiss; "TLR2 in Murine Atherosclerosis"; Semin. Immunopathol. 2008, 30:23-27.
Ropert et al., "Role of TLRs/MyD88 in Host Resistance and Pathogenesis During Protozoan Infection: Lessons from Malaria"; Semin. Immunopathol. 2008, 30:41-51.
Lee et al., "The "Polarizing—Tolerizing" Mechanism of Intestinal Epithelium: Its Relevance to Colonic Homeostasis"; Semin. Immunopathol 2008, 30:3-9.
Gao et al.; "Severe Sepsis and Toll-Like Receptors"; Semin. Immunopathol, 2008, 30:29-40.
Vijay-Kumar et al.; "Toll Like Receptor-5: Protecting the Gut from Enteric Microbes"; Semin. Immunopathol, 2008, 30:11-21.
Lenert et al.; "Structural Characterization of the Inhibitory DNA Motif for the Type A (D)-CpG-Induced Cytokine Secretion and NK-Cell Lytic Activity in Mouse Spleen Cells"; DNA Cell Biol. 2003, 22(10):621-631.
Petole et al.; "G-Rich DNA Suppresses Systemic Lupus"; J. Am. Soc. Nephrol. 2005, 16:3273-3280.
Gursel et al.; "Repetitive Elements in Mammalian Telomeres Suppress Bacterial DNA-Induced Immune Activation1"; J. Immunol. 2003, 171:1393-1400.
Shirota et al.; "Suppressive Oligodeoxynucleotides Inhibit Th1 Differentiation by Blocking IFN-gamma- and IL-12-Mediated Signaling"; Immunol., 2004, 5002-5007.
Chen et al.; "Identification of Methylated CpG Motifs as Inhibitors of the Immune Stimulatory CpG Motifs"; Gene Ther. 2001, 8:1024-1032.
Stunz et al.; "Inhibitory Oligonucleotides Specifically Block Effects of Stimulatory CpG Oligonucleotides in B Cells"; Eur. J. Immunol., 2002, 32:1212-1222.
Block et al., "Selection of Single-Stranded DNA Molecules that Bind and Inhibit Human Thrombin"; Nature, 1992, 355:564-566.
Padmanabhan et al., "The Structure of alpha-Thrombin Inhibited by a 15-Mer Single-Stranded DNA Aptamer"; J. Biol. Chem., 1993, 268:17651-17654.
Verthelyi et al.; "Human Peripheral Blood Cells Differentially Recognize and Respond to Two Distinct CpG Motifs1,2"; J. Immunol. 2001, 2372-2377.
Gursel et al.; "Differential and Competitive Activation of Human Immune Cells by Distinct Classes of CpG Oligodeoxynucleotide" J. Leukoc Biol. 2002, 71:813-820.
Krug et al.; "Identification of CpG Oligonucleotide Sequences with High Induction of IFN-alpha/beta in Plasmacytoid Dendritic Cells"; Eur J. Immunol., 2001, 31:2154-2163.
Ballas et al.; "Divergent Therapeutic and Immunologic Effects of Oligodeoxynucleotides with Distinct CpG Motifs"; J. Immunol., 2001, 167:4878-4886.
Verthelyi et al.; "CpG Oligodeoxynucleotides Protect Normal and SIV-Infected Macaques from Leishmania Infection1"; J. Immunol., 2003, 170:4717-4723.

* cited by examiner

Figure 2  Parallel Synthesis of TLR Modulation Compounds

SEQUENCE LISTING

```
<160> NUMBER OF SEQ ID NOS: 15

<210> SEQ ID NO 1
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (4)..(5)
<223> OTHER INFORMATION: 2'-O-methylribonucleoside

<400> SEQUENCE: 1
tctgacgttt tttgacgttc t                                            21

<210> SEQ ID NO 2
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (14)..(15)
<223> OTHER INFORMATION: 2'-O-methylribonucleoside
```

```
<400> SEQUENCE: 2
tctgacgttt tttgacgttc t                                              21

<210> SEQ ID NO 3
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3
tctgacgttt tttgacgttc t                                              21

<210> SEQ ID NO 4
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (4)..(5)
<223> OTHER INFORMATION: 2'-O-methylribonucleoside
<220> FEATURE:
<221> NAME/KEY: modified_base
<222> LOCATION: (14)..(15)
<223> OTHER INFORMATION: 2'-O-methylribonucleoside

<400> SEQUENCE: 4
tctgacgttt tttgacgttc t                                              21

<210> SEQ ID NO 5
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (4)..(5)
<223> OTHER INFORMATION: 2'-O-methylribonucleoside
<220> FEATURE:
<221> NAME/KEY: modified_base
<222> LOCATION: (7)..(7)
<223> OTHER INFORMATION: 2'-deoxy-7-deazaguanosine
<220> FEATURE:
<221> NAME/KEY: modified_base
<222> LOCATION: (17)..(17)
<223> OTHER INFORMATION: 2'-deoxy-7-deazaguanosine

<400> SEQUENCE: 5
tctgacgttt tttgacgttc t                                              21

<210> SEQ ID NO 6
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (7)..(7)
<223> OTHER INFORMATION: 2'-deoxy-7-deazaguanosine
<220> FEATURE:
<221> NAME/KEY: modified_base
<222> LOCATION: (14)..(15)
<223> OTHER INFORMATION: 2'-O-methylribonucleoside
```

```
<220> FEATURE:
<221> NAME/KEY: modified_base
<222> LOCATION: (17)..(17)
<223> OTHER INFORMATION: 2'-deoxy-7-deazaguanosine

<400> SEQUENCE: 6
tctgacgttt tttgacgttc t                                              21

<210> SEQ ID NO 7
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (7)..(7)
<223> OTHER INFORMATION: 2'-deoxy-7-deazaguanosine
<220> FEATURE:
<221> NAME/KEY: modified_base
<222> LOCATION: (17)..(17)
<223> OTHER INFORMATION: 2'-deoxy-7-deazaguanosine

<400> SEQUENCE: 7
tctgacgttt tttgacgttc t                                              21

<210> SEQ ID NO 8
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (4)..(5)
<223> OTHER INFORMATION: 2'-O-methylribonucleoside
<220> FEATURE:
<221> NAME/KEY: modified_base
<222> LOCATION: (7)..(7)
<223> OTHER INFORMATION: 2'-deoxy-7-deazaguanosine
<220> FEATURE:
<221> NAME/KEY: modified_base
<222> LOCATION: (14)..(15)
<223> OTHER INFORMATION: 2'-O-methylribonucleoside
<220> FEATURE:
<221> NAME/KEY: modified_base
<222> LOCATION: (17)..(17)
<223> OTHER INFORMATION: 2'-deoxy-7-deazaguanosine

<400> SEQUENCE: 8
tctgacgttt tttgacgttc t                                              21

<210> SEQ ID NO 9
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 9
ctatctgacg ttctctgt                                                  18

<210> SEQ ID NO 10
<211> LENGTH: 11
<212> TYPE: DNA
<213> ORGANISM: Artificial Sequence
```

```
<220> FEATURE:
<223> OTHER INFORMATION: Description of Artificial Sequence: Synthetic
      oligonucleotide
<220> FEATURE:
<221> NAME/KEY: modified_base
<222> LOCATION: (7)..(7)
<223> OTHER INFORMATION: 2'-deoxy-7-deazaguanosine

<400> SEQUENCE: 10
tctgacgttc t                                                              11

<210> SEQ ID NO 11
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 11
acacaccaac t                                                              11

<210> SEQ ID NO 12
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (4)..(5)
<223> OTHER INFORMATION: 2'-O-methylribonucleoside

<400> SEQUENCE: 12
tctgacgttt tttgacgttc t                                                   21

<210> SEQ ID NO 13
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (4)..(5)
<223> OTHER INFORMATION: 2'-O-methylribonucleoside
<220> FEATURE:
<221> NAME/KEY: modified_base
<222> LOCATION: (14)..(15)
<223> OTHER INFORMATION: 2'-O-methylribonucleoside

<400> SEQUENCE: 13
tctgacgttt tttgacgttc t                                                   21

<210> SEQ ID NO 14
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (4)..(5)
<223> OTHER INFORMATION: 2'-O-methylribonucleoside
<220> FEATURE:
<221> NAME/KEY: modified_base
<222> LOCATION: (7)..(7)
<223> OTHER INFORMATION: 2'-deoxy-7-deazaguanosine
```

```
<220> FEATURE:
<221> NAME/KEY: modified_base
<222> LOCATION: (17)..(17)
<223> OTHER INFORMATION: 2'-deoxy-7-deazaguanosine

<400> SEQUENCE: 14
tctgacgttt tttgacgttc t                                               21

<210> SEQ ID NO 15
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (4)..(5)
<223> OTHER INFORMATION: 2'-O-methylribonucleoside
<220> FEATURE:
<221> NAME/KEY: modified_base
<222> LOCATION: (7)..(7)
<223> OTHER INFORMATION: 2'-deoxy-7-deazaguanosine
<220> FEATURE:
<221> NAME/KEY: modified_base
<222> LOCATION: (14)..(15)
<223> OTHER INFORMATION: 2'-O-methylribonucleoside
<220> FEATURE:
<221> NAME/KEY: modified_base
<222> LOCATION: (17)..(17)
<223> OTHER INFORMATION: 2'-deoxy-7-deazaguanosine

<400> SEQUENCE: 15
tctgacgttt tttgacgttc t                                               21
```

TOLL LIKE RECEPTOR MODULATORS

RELATED APPLICATIONS

This application claims the benefit of U.S. Provisional Application Ser. No. 60/955,895, filed on Aug. 15, 2007, the contents of which are incorporated herein by reference in its entirety.

BACKGROUND OF THE INVENTION

1. Field of the Invention

A The invention relates generally to the field of immunology and immunotherapy applications using oligonucleotide-based compounds as immune modulatory agents. More particularly, the invention relates to chemically-modified oligonucleotide-based compounds that modulate immune regulation through TLRs and methods of use thereof.

2. Summary of the Related Art

The immune response involves both an innate and an adaptive response based upon the subset of cells involved in the response. For example, the T helper (Th) cells involved in classical cell-mediated functions such as delayed-type hypersensitivity and activation of cytotoxic T lymphocytes ("CTL"s) are Th1 cells, whereas the Th cells involved as helper cells for B-cell activation are Th2 cells. The type of immune response is influenced by the cytokines and chemokines produced in response to antigen exposure. Cytokines provide a means for controlling the immune response by affecting the balance of T helper 1 (Th1) and T helper 2 (Th2) cells, which directly affects the type of immune response that occurs. If the balance is toward higher numbers of Th1 cells, then a cell-mediated immune response occurs, which includes activation of cytotoxic T cells (e.g. CTLs). When the balance is toward higher numbers of Th2 cells, then a humoral or antibody immune response occurs. Each of these immune responses results in a different set of cytokines being secreted from Th1 and Th2 cells. Differences in the cytokines secreted by Th1 and Th2 cells may be the result of the different biological functions of these two T cell subsets.

Th1 cells are involved in the body's innate response to antigen (e.g. viral infections, intracellular pathogens, and tumor cells). The initial response to an antigen can be the secretion of IL-12 from antigen presenting cells (e.g. activated macrophages and dendritic cells) and the concomitant activation of Th1 cells. The result of activating Th1 cells is a secretion of certain cytokines (e.g. IL-2, IFN-gamma and other cytokines) and a concomitant activation of antigen-specific CTLs. Th2 cells are known to be activated in response to bacteria, parasites, antigens, and allergens and may mediate the body's adaptive immune response (e.g. IgM and IgG production and eosinophil activation) through the secretion of certain cytokines (e.g. IL-3, IL-4, IL-5, IL-6, IL-9, IL-10, IL-13 and other cytokines) and chemokines. Secretion of certain of these cytokines may result in B-cell proliferation and an increase in antibody production. In addition, certain of these cytokines may stimulate or inhibit the release of other cytokines (e.g. IL-10 inhibits IFN-γ secretion from Th1 cells and IL-12 from dendritic cells). The balance between Th1 and Th2 cells and the cytokines and chemokines released in response to selected stimulus can have an important role in how the body's immune system responds to disease. For example, IFN-α may inhibit hepatitis C, and MIP-1α and MIP-1β (also known as CCL3 and CCL4 respectively) may inhibit HIV-1 infection. Optimal balancing of the Th1/Th2 immune response presents the opportunity to use the immune system to treat and prevent a variety of diseases.

The Th1 immune response can be induced in mammals for example by introduction of bacterial or synthetic DNA containing unmethylated CpG dinucleotides, which immune response results from presentation of specific oligonucleotide sequences (e.g. unmethylated CpG) to receptors on certain immune cells known as pattern recognition receptors ("PRR"s). Certain of these PRRs are Toll-like receptors (TLRs).

Toll-like receptors (TLRs) are intimately involved in inducing the innate immune response in response to microbial infection. In vertebrates, a family of ten proteins called Toll-like receptors (TLR1 to TLR10) is known to recognize pathogen associated molecular patterns. Of the ten, TLR3, 7, 8, and 9 are known to localize in endosomes inside the cell and recognize nucleic acids (DNA and RNA) and small molecules such as nucleosides and nucleic acid metabolites. TLR3 and TLR9 are known to recognize nucleic acid such as dsRNA and unmethylated CpG dinucleotide present in viral and bacterial and synthetic DNA, respectively. Bacterial DNA has been shown to activate immune system and antitumor activity (Tokunaga T et al., J Natl Cancer Inst (1984) 72:955-962; Shimada S, et al., Jpn H cancer Res, 1986, 77, 808-816; Yamamoto S, et al., Jpn. J. Cancer Res, 1986, 79, 866-73; Messina, J, et al., J Immunol (1991) 147:1759-1764). Other studies using antisense oligonucleotides containing CpG dinucleotides have shown stimulation of an immune response (Zhao Q, et al., Biochem Pharmacol 1996, 26, 173-82). Subsequent studies showed that TLR9 recognizes unmethylated CpG motifs present in bacterial and synthetic DNA (Hemmi H, et al., Nature (2000) 408:740-5). Other modifications of CpG-containing phosphorothioate oligonucleotides can also affect their ability to act as modulators of immune response through TLR9 (see, e.g., Zhao et al., Biochem Pharmacol (1996) 51:173-182; Zhao et al., Biochem Pharmacol (1996) 52:1537-1544; Zhao et al., Antisense Nucleic Acid Drug Dev (1997) 7:495-502; Zhao et al., Bioorg Med Chem Lett (1999) 9:3453-3458; Zhao et al., Bioorg Med Chem Lett (2000) 10:1051-1054; Yu et al., Bioorg Med Chem Lett (2000) 10:2585-2588; Yu et al., Bioorg Med Chem Lett (2001) 11:2263-2267; and Kandimalla et al., Bioorg. Med. Chem. (2001) 9:807-813). In addition, structure activity relationship studies have allowed identification of synthetic motifs and novel DNA-based structures that induce specific immune response profiles that are distinct from those resulting from unmethylated CpG dinucleotides. (Kandimalla E R, et al., Proc Natl Acad Sci USA. (2005) 102:6925-30. Kandimalla E R, et al., Proc Natl Acad Sci USA. (2003) 100:14303-8. Cong Y P, et al., Biochem Biophys Res Commun (2003) 310:1133-9. Kandimalla E R, et al., Biochem Biophys Res Commun (2003) 306:948-53. Kandimalla E R, et al., Nucleic Acids Res. (2003) 31:2393-400. Yu D, et al., Bioorg Med Chem (2003) 11:459-64. Bhagat L, et al., Biochem Biophys Res Commun (2003) 300:853-61. Yu D, et al., Nucleic Acids Res. (2002) 30:4460-9. Yu D, et al., J Med Chem (2002) 45:4540-8. Yu D, et al., Biochem Biophys Res Commun (2002) 297:83-90. Kandimalla E R, et al., Bioconjug Chem (2002) 13:966-74. Yu D, K et al., Nucleic Acids Res. (2002) 30:1613-9. Yu D, et al., Bioorg Med Chem (2001) 9:2803-8. Yu D, et al., Bioorg Med Chem. Lett. (2001) 11:2263-7. Kandimalla E R, et al., Bioorg Med. Chem. (2001) 9:807-13. Yu D, et al., Bioorg Med Chem Let (2000) 10:2585-8, Putta M R, et al., Nucleic Acids Res (2006) 34:3231-8).

Oligonucleotides and oligodeoxynucleotides containing a ribose or deoxyribose sugar have been used in a wide variety of fields, including but not limited to diagnostic probing, PCR priming, antisense inhibition of gene expression, siRNA, microRNA, aptamers, ribozymes, and immunotherapeutic agents based on Toll-like Receptors (TLRs). More recently, many publications have demonstrated the use of oligodeoxynucleotides as immune modulatory agents and their use alone or as adjuvants in immunotherapy applications for many diseases, such as allergy, asthma, autoimmunity, inflammatory diseases, cancer, and infectious disease (Marshak-Rothstein A, Nat Rev Immunol (2006) 6:823-35).

As a result of their involvement in regulating an inflammatory response, TLRs have been shown to play a role in the pathogenesis of many diseases, including autoimmunity, infectious disease and inflammation (Papadimitraki et al. (2007) J. Autoimmun 29: 310-318; Sun et al. (2007) Inflam Allergy Drug Targets 6:223-235; Diebold (2008) Adv Drug Deliv Rev 60:813-823; Cook, D. N. et al. (2004) Nature Immunol 5:975-979; Tse and Horner (2008) Semin Immunopathol 30:53-62; Tobias & Curtiss (2008) Semin Immunopathol 30:23-27; Ropert et al. (2008) Semin Immunopathol 30:41-51; Lee et al. (2008) Semin Immunopathol 30:3-9; Gao et al. (2008) Semin Immunopathol 30:29-40; Vijay-Kumar et al. (2008) Semin Immunopathol 30:11-21). While activation of TLRs is involved in mounting an immune response, an uncontrolled stimulation of the immune system through TLRs may exacerbate certain diseases in immune compromised subjects. In recent years, several groups have shown the use of synthetic oligodeoxyoligonucleotides ("ODNs") as inhibitors of inflammatory cytokines (Lenert, P. et al. (2003) DNA Cell Biol. 22(10):621-631).

In addition, several groups have used synthetic oligodeoxynucleotides having two triplet sequences, a proximal "CCT" triplet and a distal "GGG" triplet, a poly "G" (e.g. "GGGG" or "GGG") or "GC" sequences that interact with TLR proteins to inhibit its activation and the concomitant production and release of pro-inflammatory cytokines (see for example: Lenert, P. et al. (2003) DNA Cell Biol. 22(10): 621-631; Patole, P. et al. (2005) J. Am. Soc. Nephrol. 16:3273-3280), Gursel, I., et al. (J. Immunol, 171: 1393-1400 (2003), Shirota, H., et al., J. Immunol, 173: 5002-5007 (2004), Chen, Y., et al., Gene Ther 8: 1024-1032 (2001); Stunz, L. L., Eur. J. Immunol. 32: 1212-1222 (2002; Kandimalla et al. WO2007/7047396). However, oligonucleotides containing guanosine strings have been shown to form tetraplex structures, act as aptamers and inhibit thrombin activity (Bock L C et al., Nature, 355:564-6, 1992; Padmanabhan, K et al., J Biol. Chem., 268(24):17651-4, 1993). Thus, the utility of these inhibitory oligodeoxynucleotide molecules may not be achievable in patients.

Moreover, recent studies have called into question the view that poly G containing ODNs are acting as antagonists of TLRs. For example, U.S. Pat. No. 6,426,334, Agrawal et al., demonstrate that administering CpG oligonucleotides containing "GGGG" strings will cause an increase in serum IL-12 concentration, which demonstrates TLR activation as opposed to TLR inhibition. Further, CpG oligos containing polyG sequences are known to induce immune responses through activation of TLR9 (Verthelyi D et al, J Immunol 166, 2372, 2001; Gursel M et al, J Leukoc Biol, 71, 813, 2001, Krieg A et al, Eur J Immunol, 31, 2154, 2001) and show antitumor and antiviral activities (Ballas G K et al, J Immunol, 167, 4878, 2001; Verthelyi D et al, J Immunol, 170, 4717, 2003). In addition, ODNs containing an immune stimulatory CpG motif and 4 consecutive G nucleotides (class A ODNs) induce interferon-γ production and a Th1 shift in the immune response Recently, Agrawal et al. (WO2007047396) discovered a novel class of TLR antagonists that do not possess the limitations of previously identified TLR antagonists. Such novel class of compounds effectively inhibits the activity of TLRs and block various TLR agonist activity. However, in some disease states it may be desirable to only partially antagonize TLR activity. Thus, there is a need for compounds that can antagonize TLR activity in a dose-dependent, less than full manner.

BRIEF SUMMARY OF THE INVENTION

In a first aspect, the invention provides a novel class of immune regulatory oligonucleotide compounds that reduce, but do not abolish, a TLR9-mediated immune response in a controlled manner. Such compounds have two or more TLR9-inducing moieties and one or more chemical modifications to the TLR9-inducing moiety and/or in the sequence flanking the most 5' TLR9-inducing moiety, wherein such modification inhibits the activity of the most 5' TLR9-inducing moiety, causing it to be a blocked TLR9-inducing moiety.

In one embodiment of this aspect of the invention, the compound has the structure $5'-N_m-N_1N_2C_1G_1-N_p-N_3N_4C_2G_2-N_m-3'$, wherein $C_1$ is cytosine, $G_1$ is guanosine, $C_2$ is cytosine or a cytosine derivative, and $G_2$ is guanosine or a guanosine derivative; $N_1$ and $N_2$, at each occurrence, are independently a nucleotide, 2'-substituted (e.g. 2'-O-methyl) nucleotide or nucleotide derivative or other blocking moiety that inhibits the TLR stimulatory activity of $C_1G_1$ provided that at least one N1 or N2 is a blocking moiety that inhibits the TLR stimulatory activity of $C_1G_1$; $N_3$ and $N_4$, at each occurrence, is independently a nucleotide or nucleotide derivative that does not inhibit the TLR stimulatory activity of $C_2G_2$; $N_m$, at each occurrence, is independently a nucleotide, nucleotide derivative or non-nucleotide linkage; $N_p$, at each occurrence, is independently a nucleotide or nucleotide derivative, provided that the compound contains less than 3 consecutive guanosine nucleotides; wherein m is a number from 0 to about 20, wherein p is a number from 0 to about 20; and wherein the oligonucleotide would be immune stimulatory but for the 2'-O-substituted nucleotide, nucleotide derivative or other modification that inhibits the TLR stimulatory activity of $C_1G_1$.

In another embodiment of this aspect of the invention, the compound has the structure $5'-N_m-N_1N_2C_1G_1-N_p-N_3N_4C_2G_2-N_m-3'$, wherein $C_1$ and $C_2$ are independently cytosine or a cytosine derivative, and $G_1$ and $G_2$ are independently guanosine or a guanosine derivative, wherein at least one of $C_1$ and $G_1$ is a modified nucleoside; $N_1$ and $N_2$, at each occurrence, are independently a nucleotide, 2'-substituted (e.g. 2'-O-methyl) nucleotide or nucleotide derivative or other blocking moiety that inhibits the TLR stimulatory activity of $C_1G_1$ provided that at least one N1 or N2 is a blocking moiety that inhibits the TLR stimulatory activity of $C_1G_1$; $N_3$ and $N_4$, at each occurrence, is independently a nucleotide or nucleotide derivative that does not inhibit the TLR stimulatory activity of $C_2G_2$; $N_m$, at each occurrence, is independently a nucleotide, nucleotide derivative or non-nucleotide linkage; $N_p$, at each occurrence, is independently a nucleotide or nucleotide derivative, provided that the compound contains less than 3 consecutive guanosine nucleotides; wherein m is a number from 0 to about 20, wherein p is a number from 0 to about 20; and wherein the oligonucleotide would be immune stimulatory but for the 2'-O-substituted nucleotide, nucleotide derivative or other modification that inhibits the TLR stimulatory activity of $C_1G_1$.

In a further embodiment of this aspect of the invention, the compound has the structure $5'-N_m-N_1N_2C_1G_1-N_p-N_3N_4C_2G_2-N_r-X-N_r-G_2C_2N_4N_3-N_p-G_1C_1N_2N_1-N_m-5'$, wherein $C_1$ is cytosine, $G_1$ is guanosine, $C_2$ is cytosine or a cytosine derivative, and $G_2$ is guanosine or a guanosine derivative; $N_1$ and $N_2$, at each occurrence, are independently a nucleotide, 2'-substituted (e.g. 2'-O-methyl) nucleotide or nucleotide derivative or other blocking moiety that inhibits the TLR stimulatory activity of $C_1G_1$ provided that at least one N1 or N2 is a blocking moiety that inhibits the TLR stimulatory activity of $C_1G_1$; $N_3$ and $N_4$, at each occurrence, is independently a nucleotide or nucleotide derivative that does not inhibit the TLR stimulatory activity of $C_2G_2$; $N_m$, at each occurrence, is independently a nucleotide, nucleotide derivative or non-nucleotide linkage; $N_p$, at each occurrence, is independently a nucleotide or nucleotide derivative, $N_r$, at each occurrence, is independently a nucleotide or nucleotide derivative, provided that the compound contains less than 3 consecutive guanosine nucleotides, wherein m is a number from 0 to about 20, wherein r is a number from 0 to about 20; wherein p is a number of 0 to about 20; wherein x is a non-nucleotide linker; and wherein the oligonucleotide would be immune stimulatory but for the 2'-O-substituted nucleotide, nucleotide derivative or other modification that inhibits the TLR stimulatory activity of $C_1G_1$.

In a further embodiment of this aspect of the invention, the compound has the structure 5'-$N_m$—$N_1N_2C_1G_1$-$N_p$—$N_3N_4C_2G_2$-$N_r$—X—$N_r$-$G_2C_2N_4N_3$—$N_p$-$G_1C_1N_2N_1$—$N_m$-5', wherein $C_1$ and $C_2$ are independently cytosine or a cytosine derivative, and $G_1$ and $G_2$ are independently guanosine or a guanosine derivative wherein at least one of $C_1$ and $G_1$ is a modified nucleoside; $N_1$ and $N_2$, at each occurrence, are independently a nucleotide, 2'-substituted (e.g. 2'-O-methyl) nucleotide or nucleotide derivative or other blocking moiety that inhibits the TLR stimulatory activity of $C_1G_1$ provided that at least one N1 or N2 is a blocking moiety that inhibits the TLR stimulatory activity of $C_1G_1$; $N_3$ and $N_4$, at each occurrence, is independently a nucleotide or nucleotide derivative that does not inhibit the TLR stimulatory activity of $C_2G_2$; $N_m$ at each occurrence, is independently a nucleotide, nucleotide derivative or non-nucleotide linkage; $N_p$, at each occurrence, is independently a nucleotide or nucleotide derivative, $N_r$, at each occurrence, is independently a nucleotide or nucleotide derivative, provided that the compound contains less than 3 consecutive guanosine nucleotides, wherein m is a number from 0 to about 20, wherein r is a number from 0 to about 20; wherein p is a number of 0 to about 20; wherein x is a non-nucleotide linker; and wherein the oligonucleotide would be immune stimulatory but for the 2'-O-substituted nucleotide, nucleotide derivative or other modification that inhibits the TLR stimulatory activity of $C_1G_1$.

In a second aspect the invention provides pharmaceutical compositions. These compositions comprise any one of the compounds disclosed in the first aspect of the invention and a pharmaceutically acceptable carrier.

In a third aspect the invention provides a method for reducing a TLR9-mediated immune response in a mammal, the method comprising administering to the mammal a compound or composition according to the invention in a pharmaceutically effective amount.

In a fourth aspect the invention provides a method for therapeutically treating a mammal having a disease or disorder where reducing a TLR9-mediated immune response would be beneficial. The method according to this aspect comprises administering to the mammal a compound or composition according to the invention.

In a fifth aspect the invention provides a method for preventing a disease or disorder in a mammal where reducing a TLR9-mediated immune response would be beneficial, or for diseases and disorders where controlled TLR-antagonism is desirable. The method according to this aspect comprises administering to the mammal a compound or composition according to the invention.

BRIEF DESCRIPTION OF THE DRAWINGS

FIG. 3 more generally demonstrates that the novel inhibitory oligonucleotides will function as antagonists as lower concentrations and as agonists at higher concentrations, effectively controlling their inhibitory activity.

FIG. 4 more generally demonstrates that the novel inhibitory oligonucleotides will function as antagonists at lower concentrations and as agonists at higher concentrations.

FIG. 5 more generally demonstrates that the novel inhibitory oligonucleotides will function as antagonists as lower concentrations and as agonists at higher concentrations, effectively controlling their inhibitory activity.

FIG. 6 more generally demonstrates that the novel inhibitory oligonucleotides will function as antagonists as lower concentrations and as agonists at higher concentrations, effectively controlling their inhibitory activity.

FIG. 7 more generally demonstrates that the novel inhibitory oligonucleotides will function as antagonists as lower concentrations and as agonists at higher concentrations, effectively controlling their inhibitory activity.

DETAILED DESCRIPTION OF THE PREFERRED EMBODIMENTS

Figure 1:
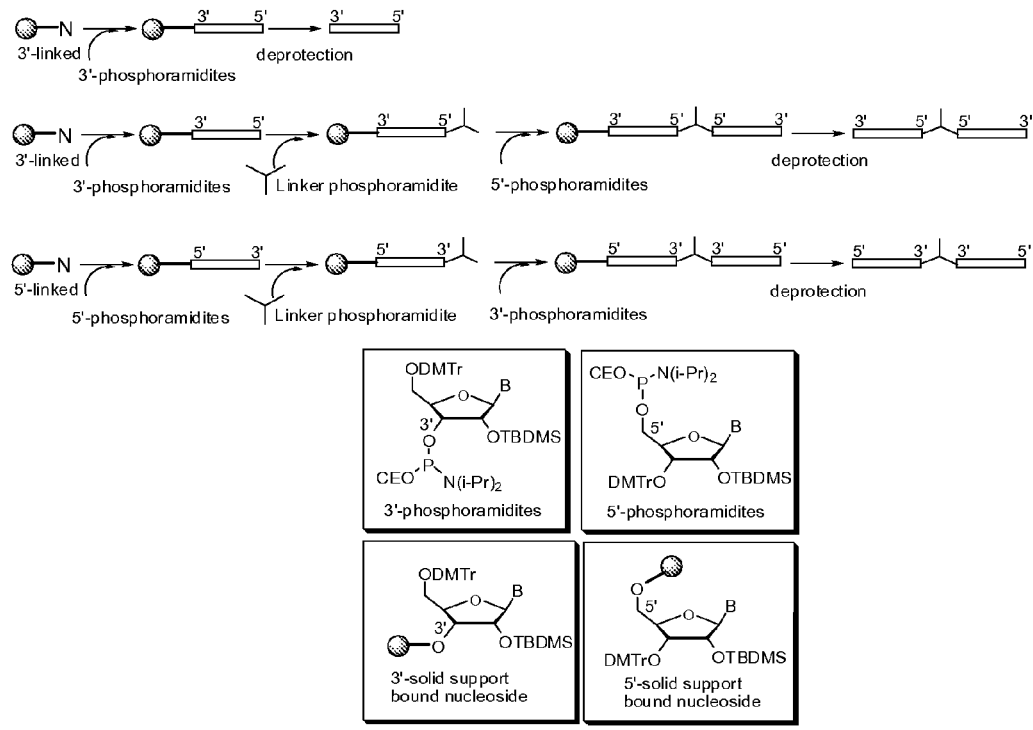
FIG. 1 is a synthetic scheme for the linear synthesis of compounds of the invention. DMTr=4,4'-dimethoxytrityl; CE=cyanoethyl.

The invention relates to the therapeutic use of oligonucleotides as immune modulatory agents for immunotherapy applications. Specifically, the invention provides oligonucleotide-based compounds that modulate the immune response through TLR9. By reducing, but not abolishing TLR9-mediated immune responses, the invention provides compounds and methods that may be useful for treating or preventing a variety of diseases or disorders, including those that have an autoimmune component where administration of a dosage controlled antagonist of TLR9 would be beneficial. The issued patents, patent applications, and references that are cited herein are hereby incorporated by reference to the same extent as if each was specifically and individually indicated to be incorporated by reference. In the event of inconsistencies between any teaching of any reference cited herein and the present specification, the latter shall prevail for purposes of the invention.

The foregoing and other objects of the present invention, the various features thereof, as well as the invention itself may be more fully understood from the following description, when read together with the accompanying drawings in which:

The term "2'-substituted nucleoside" or "2'-substituted arabinoside" generally includes nucleosides or arabinonucleosides in which the hydroxyl group at the 2' position of a pentose or arabinose moiety is substituted to produce a 2'-substituted or 2'-O-substituted ribonucleoside. In certain embodiments, such substitution is with a lower hydrocarbyl group containing 1-6 saturated or unsaturated carbon atoms, with a halogen atom, or with an aryl group having 6-10 carbon atoms, wherein such hydrocarbyl, or aryl group may be unsubstituted or may be substituted, e.g., with halo, hydroxy, trifluoromethyl, cyano, nitro, acyl, acyloxy, alkoxy, carboxyl, carboalkoxy, or amino groups. Examples of 2'-O-substituted ribonucleosides or 2'-O-substituted-arabinosides include, without limitation 2'-amino, 2'-fluoro, 2'-allyl, 2'-O-alkyl and 2'-propargyl ribonucleosides or arabinosides, 2'-O-methylribonucleosides or 2'-O-methylarabinosides and 2'-O-methoxyethoxyribonucleosides or 2'-O-methoxyethoxyarabinosides.

The term "3'", when used directionally, generally refers to a region or position in a polynucleotide or oligonucleotide 3' (toward the 3' position of the oligonucleotide) from another region or position in the same polynucleotide or oligonucleotide.

The term "5'", when used directionally, generally refers to a region or position in a polynucleotide or oligonucleotide 5' (toward the 5' position of the oligonucleotide) from another region or position in the same polynucleotide or oligonucleotide.

The term "about" generally means that the exact number is not critical. Thus, the number of nucleoside residues in the oligonucleotides is not critical, and oligonucleotides having one or two fewer nucleoside residues, or from one to several additional nucleoside residues are contemplated as equivalents of each of the embodiments described above.

The term "airway inflammation" generally includes, without limitation, inflammation in the respiratory tract caused by allergens, including asthma.

The term "allergen" generally refers to an antigen or antigenic portion of a molecule, usually a protein, which elicits an allergic response upon exposure to a subject. Typically the subject is allergic to the allergen as indicated, for instance, by the wheal and flare test or any method known in the art. A molecule is said to be an allergen even if only a small subset of subjects exhibit an allergic (e.g., IgE) immune response upon exposure to the molecule.

The term "allergy" generally includes, without limitation, food allergies, respiratory allergies, and skin allergies.

The term "antigen" generally refers to a substance that is recognized and selectively bound by an antibody or by a T cell antigen receptor. Antigens may include but are not limited to peptides, proteins, nucleosides, nucleotides and combinations thereof. Antigens may be natural or synthetic and generally induce an immune response that is specific for that antigen.

The term "autoimmune disorder" generally refers to disorders in which "self" antigen undergo attack by the immune system.

The term "carrier" generally encompasses any excipient, diluent, filler, salt, buffer, stabilizer, solubilizer, oil, lipid, lipid containing vesicle, microspheres, liposomal encapsulation, or other material well known in the art for use in pharmaceutical formulations. It will be understood that the characteristics of the carrier, excipient, or diluent will depend on the route of administration for a particular application. The preparation of pharmaceutically acceptable formulations containing these materials is described in, e.g., *Remington's Pharmaceutical Sciences*, 18th Edition, ed. A. Gennaro, Mack Publishing Co., Easton, Pa., 1990.

The term "co-administration" generally refers to the administration of at least two different substances sufficiently close in time to modulate an immune response. Preferably, co-administration refers to simultaneous administration of at least two different substances.

The term a "pharmaceutically effective amount" generally refers to an amount sufficient to affect a desired biological effect, such as a beneficial result, including, without limitation, prevention, inhibition, diminution, amelioration or elimination of signs or symptoms of a disease or disorder. Thus, a "pharmaceutically effective amount" will depend upon the context in which it is being administered. A pharmaceutically effective amount may be administered in one or more prophylactic or therapeutic administrations.

The term "prophylactically effective amount" generally refers to an amount sufficient to prevent, reduce or inhibit the development of an undesired biological effect.

The term "in combination with" generally means administering a compound according to the invention and another agent useful for treating the disease or condition that does not diminish TLR9 antagonist effect of the compound in the course of treating the same disease in the same patient. Such administration may be done in any order, including simultaneous administration, as well as temporally spaced order from a few seconds up to several days apart. Such combination treatment may also include more than a single administration of the compound according to the invention and/or independently the other agent. The administration of the compound according to the invention and the other agent may be by the same or different routes.

The term "individual" or "subject" generally refers to a mammal, such as a human. Mammals generally include, but are not limited to, humans, non-human primates, rats, mice, cats, dogs, horses, cattle, cows, pigs, sheep and rabbits.

The term "linear synthesis" generally refers to a synthesis that starts at one end of an oligonucleotide and progresses linearly to the other end. Linear synthesis permits incorporation of either identical or non-identical (in terms of length, base composition and/or chemical modifications incorporated) monomeric units into an oligonucleotide.

The term "modified" or "derivative" when used in the context of a nucleoside or nucleotide generally refer to a nucleoside that includes a modified heterocyclic base, a modified sugar moiety or any combination thereof or a nucleotide having any such modifications or a modified phosphate. In some embodiments, the modified nucleoside is a non-natural pyrimidine or purine nucleoside, as herein described. For purposes of the invention, a modified nucleoside, a pyrimidine or purine analog or non-naturally occurring pyrimidine or purine can be used interchangeably and refers to a nucleoside that includes a non-naturally occurring base and/or non-naturally occurring sugar moiety. For purposes of the invention, a base is considered to be non-natural if it is not guanine, cytosine, adenine, thymine or uracil.

The term "modulation" or "modulatory" generally refers to change, such as a decrease in a response or qualitative difference in a TLR9-mediated response.

The term "linker" generally refers to any moiety that can be attached to an oligonucleotide by way of covalent or non-covalent bonding through a sugar, a base, or the backbone. The linker can be used to attach two or more nucleosides or can be attached to the 5' and/or 3' terminal nucleotide in the oligonucleotide. Such linker can be either a non-nucleotidic linker or a nucleotidic linker.

The term "non-nucleotidic linker" generally refers to a chemical moiety other than a nucleotidic linkage that can be attached to an oligonucleotide by way of covalent or non-covalent bonding. Preferably such non-nucleotidic linker is from about 2 angstroms to about 200 angstroms in length, and may be either in a cis or trans orientation.

The term "nucleotidic linkage" generally refers to a chemical linkage to join two nucleosides through their sugars (e.g. 3'-3', 2'-3', 2'-5', 3'-5') consisting of a phosphorous atom and a charged, or neutral group (e.g., phosphodiester, phosphorothioate, phosphorodithioate, alkylphosphonate or phosphoramidate) between adjacent nucleosides.

The term "oligonucleotide-based compound" refers to a polynucleoside formed from a plurality of linked nucleoside units. Such oligonucleotides can be obtained from existing nucleic acid sources, including genomic or cDNA, but are preferably produced by synthetic methods. In preferred embodiments each nucleoside unit includes a heterocyclic base and a pentofuranosyl, trehalose, arabinose, 2'-deoxy-2'-substitutedarabinose, 2'-O-substitutedarabinose or hexose sugar group. The nucleoside residues can be coupled to each other by any of the numerous known internucleoside linkages. Such internucleoside linkages include, without limitation, phosphodiester, phosphorothioate, phosphorodithioate, alkylphosphonate, alkylphosphonothioate, phosphotriester, phosphoramidate, siloxane, carbonate, carboalkoxy, acetamidate, carbamate, morpholino, borano, thioether, bridged phosphoramidate, bridged methylene phosphonate, bridged phosphorothioate, and sulfone internucleoside linkages. The term "oligonucleotide-based compound" also encompasses polynucleosides having one or more stereospecific internucleoside linkage (e.g., $(R_P)$- or $(S_P)$-phosphorothioate, alkylphosphonate, or phosphotriester linkages). As used herein, the terms "oligonucleotide" and "dinucleotide" are expressly intended to include polynucleosides and dinucleosides having any such internucleoside linkage, whether or not the linkage comprises a phosphate group. In certain preferred embodiments, these internucleoside linkages may be phosphodiester, phosphorothioate, or phosphorodithioate linkages, or combinations thereof.

The term "peptide" generally refers to polypeptides that are of sufficient length and composition to affect a biological response, e.g., antibody production or cytokine activity whether or not the peptide is a hapten. The term "peptide" may include modified amino acids (whether or not naturally or non-naturally occurring), where such modifications include, but are not limited to, phosphorylation, glycosylation, pegylation, lipidization and methylation.

The term "physiologically acceptable" generally refers to a material that does not interfere with the effectiveness of a compound according to the invention, and that is compatible with a biological system such as a cell, cell culture, tissue, or organism. Preferably, the biological system is a living organism, such as a vertebrate.

The term "TLR9 antagonist" generally refers to an oligonucleotide-based compound that is able to prevent or reduce immune stimulation mediated by TLR9.

The term "TLR9-inducing moiety" refers to a dinucleotide moiety which, in the context of an oligonucleotide-based compound, induces a TLR9 mediated immune response. In preferred embodiments, the dinucleotide has the structure Y-Z, wherein Y is cytidine, 2' deoxycytidine, arabinocytidine, 2'-deoxy-2'-substitutedarabinocytidine, 2'-O-substitutedarabinocytidine, 2'-deoxy-5-hydroxycytidine, 2'-deoxy-N4-alkyl-cytidine, 2'-deoxy-4-thiouridine or other non-natural pyrimidine nucleoside; and Z is guanosine, 2'-deoxyguanosine, 2' deoxy-7-deazaguanosine, 2'-deoxy-6-thioguanosine, arabinoguanosine, 2'-deoxy-2'substituted-arabinoguanosine, 2'-O-substituted-arabinoguanosine, 2'-deoxyinosine, or other non-natural purine nucleoside.

The term "blocked TLR9-inducing moiety" refers to a TLR9-inducing moiety that would have TLR9 agonistic activity but for that fact that it has been functionally blocked or inhibited from inducing TLR9 mediated immune response through modification(s) of the TLR9-inducing moiety itself and/or by one or more chemical modification within the oligonucleotide based compound. Blocking moieties that inhibit the activity of a TLR9-inducing moiety include, but not limited to, 2'-OMe-ribonucleosides, 3'-OMe-ribonucleosides, 3-nitropyrrole, 5-nitroindole, dU, β-L-deoxynucleosides, α-deoxynucleosides, abasic nucleoside, propanediol linker, amino linker, isopropoxyl, glycerol linker, 2'-5'-DNA, 2'-5' RNA, and P-Me DNA The term "treatment" generally refers to an approach intended to obtain a beneficial or desired result, which may include alleviation of symptoms, or delaying or ameliorating a disease progression.

In a first aspect, the invention provides a novel class of immune regulatory oligonucleotide compounds that reduce, but do not abolish, a TLR9-mediated immune response in a controlled manner. Such compounds have two or more TLR9-inducing moieties and one or more chemical modifications to the TLR9-inducing moiety and/or in the sequence flanking the most 5' TLR9-inducing moiety, wherein such modification inhibits the activity of the most 5' TLR9-inducing moiety, causing it to be a blocked TLR9-inducing moiety.

In one embodiment of this aspect of the invention, the compound has the structure 5'-$N_m$—$N_1N_2C_1G_1$-$N_p$—$N_3N_4C_2G_2$-$N_m$-3', wherein $C_1$ is cytosine, $G_1$ is guanosine, $C_2$ is cytosine or a cytosine derivative, and $G_2$ is guanosine or a guanosine derivative; $N_1$ and $N_2$, at each occurrence, are independently a nucleotide, 2'-substituted (e.g. 2'-O-methyl) nucleotide or nucleotide derivative or other blocking moiety that inhibits the TLR stimulatory activity of $C_1G_1$ provided that at least one N1 or N2 is a blocking moiety that inhibits the TLR stimulatory activity of $C_1G_1$; $N_3$ and $N_4$, at each occurrence, is independently a nucleotide or nucleotide derivative that does not inhibit the TLR stimulatory activity of $C_2G_2$; $N_m$, at each occurrence, is independently a nucleotide, nucleotide derivative or non-nucleotide linkage; $N_p$, at each occurrence, is independently a nucleotide or nucleotide derivative, provided that the compound contains less than 3 consecutive guanosine nucleotides; wherein m is a number from 0 to about 20, wherein p is a number from 0 to about 20; and wherein the oligonucleotide would be immune stimulatory but for the 2'-O-substituted nucleotide, nucleotide derivative or other modification that inhibits the TLR stimulatory activity of $C_1G_1$. In this embodiment, the first TLR9-inducing moiety is 5' to the second TLR9-inducing moiety, wherein the first TLR9-inducing moiety is a blocked TLR9-inducing moiety, which acts as a TLR9 antagonist, and wherein the second TLR9-inducing moiety is not blocked.

In another embodiment of this aspect of the invention, the compound has the structure 5'-$N_m$—$N_1N_2C_1G_1$-$N_p$—$N_3N_4C_2G_2$-$N_m$-3', wherein $C_1$ and $C_2$ are independently cytosine or a cytosine derivative, and $G_1$ and $G_2$ are independently guanosine or a guanosine derivative, wherein at least one of $C_1$ and $G_1$ is a modified nucleoside; $N_1$ and $N_2$, at each occurrence, are independently a nucleotide, 2'-substituted (e.g. 2'-O-methyl) nucleotide or nucleotide derivative or other blocking moiety that inhibits the TLR stimulatory activity of $C_1G_1$ provided that at least one N1 or N2 is a blocking moiety that inhibits the TLR stimulatory activity of $C_1G_1$; $N_3$ and $N_4$, at each occurrence, is independently a nucleotide or nucleotide derivative that does not inhibit the TLR stimulatory activity of $C_2G_2$; $N_m$, at each occurrence, is independently a nucleotide, nucleotide derivative or non-nucleotide linkage; $N_p$, at each occurrence, is independently a nucleotide or nucleotide derivative, provided that the compound contains less than 3 consecutive guanosine nucleotides; wherein m is a number from 0 to about 20, wherein p is a number from 0 to about 20; and wherein the oligonucleotide would be immune stimulatory but for the 2'-O-substituted nucleotide, nucleotide derivative or other modification that inhibits the TLR stimulatory activity of $C_1G_1$. In this embodiment, the first TLR9-inducing moiety is 5' to the second TLR9-inducing moiety, wherein the first TLR9-inducing moiety is a blocked TLR9-inducing moiety, which acts as a TLR9 antagonist, and wherein the second TLR9-inducing moiety is not blocked.

In a further embodiment of this aspect of the invention, the invention provides an immune regulatory oligonucleotide comprising at least two oligonucleotides linked at their 3' ends, or an internucleoside linkage or a functionalized nucleobase or sugar to a non-nucleotidic linker. For example, a compound of this embodiment has the structure 5'-$N_m$—$N_1N_2C_1G_1$-$N_p$—$N_3N_4C_2G_2$-$N_r$—X—$N_r$-$G_2C_2N_4N_3$—$N_p$-$G_1C_1N_2N_1$—$N_m$-5' wherein $C_1$ is cytosine, $G_1$ is guanosine, $C_2$ is cytosine or a cytosine derivative, and $G_2$ is guanosine or a guanosine derivative; $N_1$ and $N_2$, at each occurrence, are independently a nucleotide, 2'-substituted (e.g. 2'-O-methyl) nucleotide or nucleotide derivative or other blocking moiety that inhibits the TLR stimulatory activity of $C_1G_1$ provided that at least one N1 or N2 is a blocking moiety that inhibits the TLR stimulatory activity of $C_1G_1$; $N_3$ and $N_4$, at each occurrence, is independently a nucleotide or nucleotide derivative that does not inhibit the TLR stimulatory activity of $C_2G_2$; $N_m$, at each occurrence, is independently a nucleotide, nucleotide derivative or non-nucleotide linkage; $N_p$, at each occurrence, is independently a nucleotide or nucleotide derivative, $N_r$, at each occurrence, is independently a nucleotide or nucleotide derivative, provided that the compound contains less than 3 consecutive guanosine nucleotides, wherein m is a number from 0 to about 20, wherein r is a number from 0 to about 20; wherein p is a number of 0 to about 20; wherein x is a non-nucleotidic linker; and wherein the oligonucleotide would be immune stimulatory but for the 2'-O-substituted nucleotide, nucleotide derivative or other modification that inhibits the TLR stimulatory activity of $C_1G_1$.

In another embodiment, the invention provides an immune regulatory oligonucleotide comprising at least two oligonucleotides linked at their 3' ends, or an internucleoside linkage or a functionalized nucleobase or sugar to a non-nucleotidic linker. For example, a compound of this embodiment has the structure 5'-$N_m$—$N_1N_2C_1G_1$-$N_p$—$N_3N_4C_2G_2$-$N_r$—X—$N_r$-$G_2C_2N_4N_3$—$N_p$-$G_1C_1N_2N_1$—$N_m$-5', wherein $C_1$ and $C_2$ are independently cytosine or a cytosine derivative, and $G_1$ and $G_2$ are independently guanosine or a guanosine derivative wherein at least one of $C_1$ and $G_1$ is a modified nucleoside; $N_1$ and $N_2$, at each occurrence, are independently a nucleotide, 2'-substituted (e.g. 2'-O-methyl) nucleotide or nucleotide derivative or other blocking moiety that inhibits the TLR stimulatory activity of $C_1G_1$ provided that at least one N1 or N2 is a blocking moiety that inhibits the TLR stimulatory activity of $C_1G_1$; $N_3$ and $N_4$, at each occurrence, is independently a nucleotide or nucleotide derivative that does not inhibit the TLR stimulatory activity of $C_2G_2$; $N_m$, at each occurrence, is independently a nucleotide, nucleotide derivative or non-nucleotide linkage; $N_p$, at each occurrence, is independently a nucleotide or nucleotide derivative, $N_r$, at each occurrence, is independently a nucleotide or nucleotide derivative, provided that the compound contains less than 3 consecutive guanosine nucleotides, wherein m is a number from 0 to about 20, wherein r is a number from 0 to about 20; wherein p is a number of 0 to about 20; wherein x is a non-nucleotidic linker; and wherein the oligonucleotide would be immune stimulatory but for the 2'-O-substituted nucleotide, nucleotide derivative or other modification that inhibits the TLR stimulatory activity of $C_1G_1$.

Such embodiments of the invention may have at least one accessible 5' end. It has been determined that this structure provides further stability (e.g. inhibition of exonuclease activity) to the immune regulatory oligonucleotide compounds. The 5'-terminus of the immune regulatory oligonucleotide is not modified in such a way as to prevent the immune regulatory oligonucleotide compound from modulating an immune response through TLR9.

In another embodiment of this aspect of the invention comprises at least two oligoribonucleotides, wherein at least one of Domain A, B, C, and D comprises a TLR9 antagonist with at least one TLR9-inducing moiety and a blocked TLR9-inducing moiety 5' to the TLR-inducing moiety, wherein the immune modulatory compound has a structure including, but not limited to, those as detailed in Formulas I-X in Table 1.

TABLE 1

| Oligoribonucleotide Formulas I-X | |
|---|---|
| Formula I | 5' Domain A 3'—X—3' Domain B 5' |
| Formula IIa | 5' Domain A 3'—X—5' Domain B 3'—X—3' Domain C 5' |
| Formula IIb | 3' Domain A 5'—X—5' Domain B 3'—X—3' Domain C 5' |
| Formula III | 5' Domain A 3'—X—5' Domain B 3'—X—5' Domain C 3'—X—3' Domain D 5' |

TABLE 1-continued

Oligoribonucleotide Formulas I-X

Formula IV — diagram with 5' Domain A, 3'-5' Domain B linked via X, 3'-3' Domain C linked via X, 5' Domain D (branched hairpin structure)

Formula V — 5' Domain A 3'—X—3' Domain B 5', with a sphere attached below X

Formula VI — branched structure with two X linkers joining four strands with 5' and 3' labeled ends Formula VII — 5' Domain A 3', 3'-5' Domain B, joined via X to 3' Domain C 5'

Formula VIII — 5'━━━X 3' / 3' X━━━5' (two strands linked by X)

Formula IX — 5' Domain A —X— Domain B 3' / 3' Domain B —X— Domain A 5'

Formula X — [5' Domain A —X— Domain B 3' 5' Domain A —X— Domain B 3' / 3' Domain B —X— Domain A 5']$_n$ Domains A, B, C, and D may be independently from about 8 to about 30 nucleotides, more preferably from about 10 to about 21 nucleotides. Domains A, B, C, and/or D may or may not be identical. Domains A, B, C, and D may independently be 5'-3' or 2'-5' RNA having or not having a self-complementary domain, a homo or hetero ribonucleotide sequence, or a linker. "n" may be from 1 to an unlimited number.

"X" is a linker joining or capping Domains A, B, C, and/or D that may be through a 3' or 5' linkage, a phosphate group, a non-RNA nucleotide, or a non-nucleotidic linker that may be aliphatic, aromatic, aryl, cyclic, chiral, achiral, a peptide, a carbohydrate, a lipid, a fatty acid, mono- tri- or hexapolyethylene glycol, or a heterocyclic moiety, or combinations thereof.

In a further embodiment, the invention provides an immune regulatory oligonucleotide compound comprising at least two oligonucleotides linked by a non-nucleotide linker, wherein the sequences of the immune modulatory oligonucleotides may be at least partially self-complementary. As would be recognized by one skilled in the art, the complementary sequence of the oligonucleotides allows for intermolecular hydrogen bonding thereby giving the oligonucleotides secondary structure. Additional oligonucleotides can bind together thereby creating a chain, or multimers, of oligonucleotides according to the invention.

Compounds according to this aspect act as antagonists of TLR9 at a first dosage and act as partial agonists of TLR9 at a second, higher dosage. Without wishing to be bound by theory, Applicants believe that, at lower concentrations, compounds according to this aspect bind TLR9 primarily via the first (most 5') TLR9-inducing moiety. This is because TLR9 is believed to interact with oligonucleotide-based compounds initially at their 5' end(s). Since the activity of the first TLR9-inducing moiety is blocked, the compound acts as a TLR9 antagonist at dosages at which TLR9 interacts with the compound primarily at the first (most 5') TLR9-inducing moiety. However, at higher concentrations, it is believed that the first (most 5') TLR9-inducing moiety becomes saturated, and that TLR9 begins to interact with the compound at a second (more 3') TLR9-inducing moiety. Because the second (more 3') TLR9-inducing moiety is not blocked, the compound then begins to act as a TLR9 agonist.

The advantage of compounds according to this aspect is that while a TLR9 mediated immune responses are reduced at lower dosages of the compound, it is not abolished at higher dosages because the compound at that point begins to acts as a TLR9 agonist. Thus, compounds according to this aspect are self-regulating in the extent of their antagonism of TLR9.

In some embodiments according to this aspect of the invention, the compound has an immunomer structure, as described in U.S. Pat. No. 7,276,489.

In some embodiments, the linear oligonucleotides or one or more branched oligonucleotides each independently have from about 8 to about 30 nucleoside residues. Thus in certain embodiments the oligonucleotide can independently be 8, 9, 10, 11, 12, 13, 14, 15, 16, 17, 18, 19, 20, 21, 22, 23, 24, 25, 26, 27, 28, 29 or 30 nucleotides long. Preferably the oligonucleotide is from about 11 to about 25 nucleoside residues, more preferably from about 16 to about 21 nucleoside residues. In some embodiments, the immune modulatory oligonucleotides comprise 21 oligonucleotides. Certain preferred embodiments comprise 42 nucleotides. Preferably, the TLR9 antagonist compound comprises at least one phosphodiester, phosphorothioate, or phosphorodithioate internucleoside linkage.

In preferred embodiments each nucleoside unit includes a heterocyclic base and a pentofuranosyl, 2'-O-substituted pentofuranosyl, trehalose, arabinose, 2'-deoxy-2'-substituted arabinose, 2'-O-substituted ribose or arabinose or a hexose sugar group. The nucleoside residues can be coupled to each other by any of the numerous known internucleoside linkages. Such internucleoside linkages include, without limitation, phosphodiester, phosphorothioate, phosphorodithioate, alkylphosphonate, alkylphosphonothioate, phosphotriester, phosphoramidate, siloxane, carbonate, carboalkoxy, acetamidate, carbamate, morpholino, borano, thioether, bridged phosphoramidate, bridged methylene phosphonate, bridged phosphorothioate, and sulfone internucleoside linkages. Possible sites of conjugation for the nucleotide are indicated in Formula XI, below, wherein B represents a heterocyclic base.

Formula XI

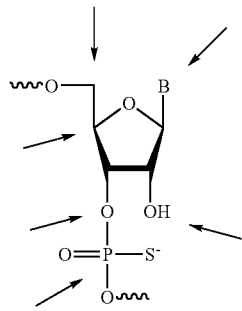

The TLR9 antagonist compounds of the invention can further include naturally occurring ribonucleosides, modified ribonucleosides or mixtures thereof.

Some chemical modifications to the heterocyclic bases include, but are not limited to, guanine analogues such as 7-deaza-G, ara-G, 6-thio-G, Inosine, Iso-G, loxoribine, TOG (7-thio-8-oxo)-G, 8-bromo-G, 8-hydroxy-G, 5-aminoformycin B, Oxoformycin, 7-methyl-G, 9-p-chlorophenyl-8-aza-G, 9-phenyl-G, 9-hexyl-guanine, 7-deaza-9-benzyl-G, 6-Chloro-7-deazaguanine, 6-methoxy-7-deazaguanine, 8-Aza-7-deaza-G(PPG), 2-(Dimethylamino) guanosine, 7-Methyl-6-thioguanosine, 8-Benzyloxyguanosine, 9-Deazaguanosine, and 1-(B-D-furanosyl)-2-oxo-7-deaza-8-methyl-purine. Chemical modifications also include, but are not limited to, adenine analogues such as 9-benzyl-8-hydroxy-2-(2-methoxyethoxy)adenine, 2-Amino-N2-O—, methyladenosine, 8-Aza-7-deaza-A, 7-deaza-A, Vidarabine, 2-Aminoadenosine, N1-Methyladenosine, 8-Azaadenosine, 5-Iodotubercidin. Chemical modifications also include, but are not limited to, cytosine analogues, such as 2'-deoxy-5-hydroxycytidine and 2'-deoxy-N4-alkyl-cytidine. Chemical modifications also include, but are not limited to, uracil analogues such as 4-thio-U.

The TLR9 antagonist compounds according to the invention include compounds that comprise at least two oligonucleotides linked covalently or non-covalently at their 3'- or 2'-ends or functionalized ribose or deoxyribose (including substituted forms) or functionalized nucleobase via a non-nucleotidic or a nucleotidic linker. Several examples of linkers are set forth in Table 2. Non-covalent linkages include, but are not limited to, electrostatic interaction, hydrophobic interactions, π-stacking interactions and hydrogen bonding.

In yet other embodiments, the non-nucleotidic linker is an organic moiety having functional groups that permit attachment to the oligonucleotide. Such attachment preferably is by a stable covalent linkage. As a non-limiting example, the linker may be attached to any suitable position on the nucleotide. In some preferred embodiments, the linker is attached to the 3'-hydroxyl. In such embodiments, the linker preferably comprises a hydroxyl functional group, which preferably is attached to the 3'-hydroxyl by means of a phosphate-based linkage like, phosphodiester, phosphorothioate, phosphorodithioate, methylphosphonate or non-phosphate-based linkages.

In some embodiments, the non-nucleotidic linker is a small molecule, macromolecule or biomolecule, including, without limitation, polypeptides, antibodies, lipids, antigens, allergens, and oligosaccharides. In some other embodiments, the non-nucleotidic linker is a small molecule. For purposes of the invention, a small molecule is an organic moiety having a molecular weight of less than 1,000 Da. In some embodiments, the small molecule has a molecular weight of less than 750 Da.

In some embodiments, the small molecule is an aliphatic or aromatic hydrocarbon, either of which optionally can include, either in the linear chain connecting the oligonucleotides or appended to it, one or more functional groups including, but not limited to, hydroxy, amino, thiol, thioether, ether, amide, thioamide, ester, urea or thiourea. The small molecule can be cyclic or acyclic. Examples of small molecule linkers include, but are not limited to, amino acids, carbohydrates, cyclodextrins, adamantane, cholesterol, haptens and antibiotics. However, for purposes of describing the non-nucleotidic linker, the term "small molecule" is not intended to include a nucleoside.

In some embodiments, the non-nucleotidic linker is an alkyl linker or amino linker. The alkyl linker may be branched or unbranched, cyclic or acyclic, substituted or unsubstituted, saturated or unsaturated, chiral, achiral or racemic mixture. The alkyl linkers can have from about 2 to about 18 carbon atoms. In some embodiments such alkyl linkers have from about 3 to about 9 carbon atoms. Some alkyl linkers include one or more functional groups including, but not limited to, hydroxy, amino, thiol, thioether, ether, amide, thioamide, ester, urea, and thioether. Such alkyl linkers can include, but are not limited to, 1-propanol, 1,2 propanediol, 1,3 propanediol, 1,2,3, propanetriol, triethylene glycol, hexaethylene glycol, polyethylene glycol linkers (e.g. [—O—CH2-CH2-]$_n$ (n=1-9)), methyl linkers, ethyl linkers, propyl linkers, butyl linkers, or hexyl linkers. In some embodiments, such alkyl linkers may include peptides or amino acids.

In some embodiments, the non-nucleotidic linker may include, but are not limited to, those listed in Table 2.

TABLE 2
Representative Non-nucleotidic Linkers
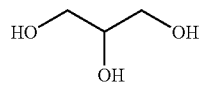
Glycerol (1,2,3-Propanetriol)
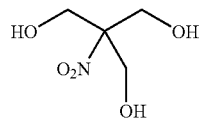
1,1,1-Tris(hydroxymethyl)nitromethane
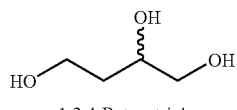
1,2,4-Butanetriol
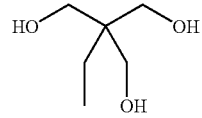
1,1,1-Tris(hydroxymethyl)propane
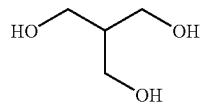
2-(hydroxymethyl)-1,3-propanediol
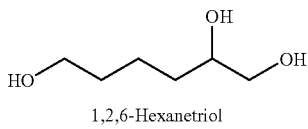
1,2,6-Hexanetriol
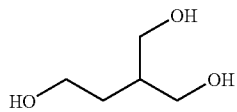
2-(hydroxymethyl)1,4-butanediol
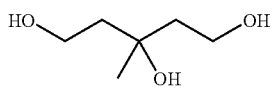
3-Methyl-1,3,5-pentanetriol
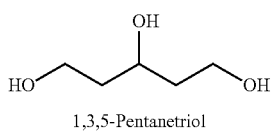
1,3,5-Pentanetriol
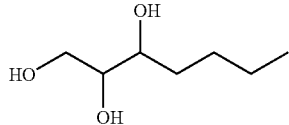
1,2,3-Heptanetriol TABLE 2-continued
Representative Non-nucleotidic Linkers
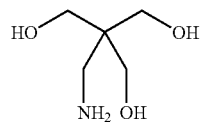
2-Amino-2-(hydroxymethyl)-1,3-propanediol
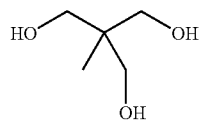
1,1,1-Tris(hydroxymethyl)ethane
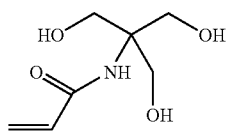
N-[Tris(hydroxymethyl)methyl]acrylamide
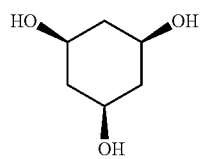
cis-1,3,5-Cyclohexanetriol
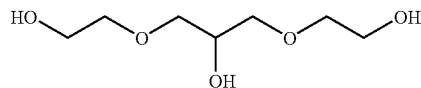
1,3-Di(hydroxyethoxy)-2-hydroxyl-propane
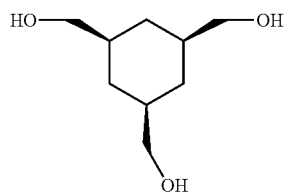
cis-1,3,5-Tri(hydroxymethyl)cyclohexane
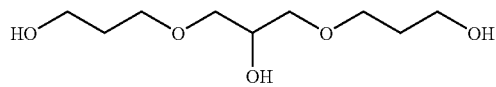
1,3-Di(hydroxypropoxy)-2-hydroxyl-propane
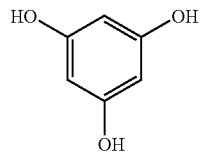
1,3,5-Trihydroxyl-benzene
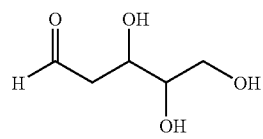
2-Deoxy-D-ribose TABLE 2-continued
Representative Non-nucleotidic Linkers
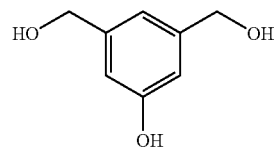
3,5,-Di(hydroxymethyl)phenol
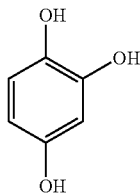
1,2,4,-Trihydroxyl-benzene
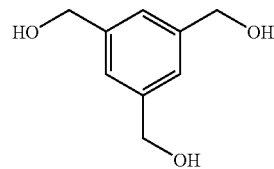
1,3,5,-Tri(hydroxymethyl)benzene
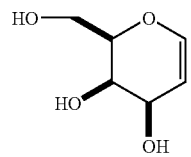
D-Galactoal
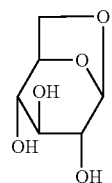
1,6-anhydro-β-D-Glucose
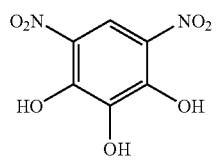
4,6-Nitropyrogallol
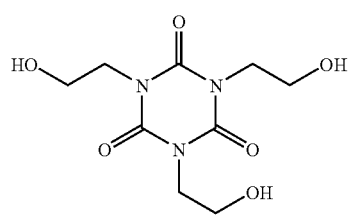
1,3,5-Tris(2-hydroxyethyl)-Cyanuric acid

TABLE 2-continued
Representative Non-nucleotidic Linkers
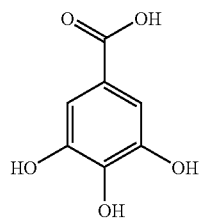
Gallic acid
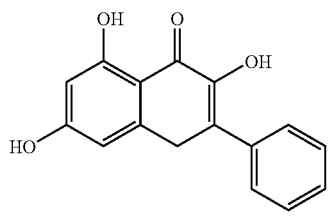
3,5,7-Trihydroxyflavone
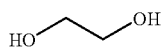
Ethylene glycol
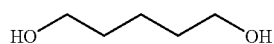
1,5-Pentanediol
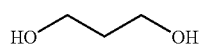
1,3-Propanediol
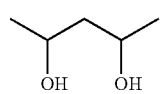
2,4-Pentanediol
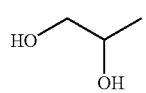
1,2-Propanediol
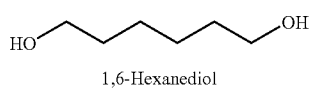
1,6-Hexanediol
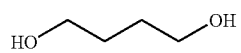
1,4-Butanediol
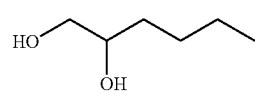
1,2-Hexanediol
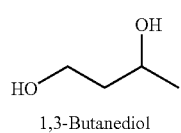
1,3-Butanediol TABLE 2-continued
Representative Non-nucleotidic Linkers
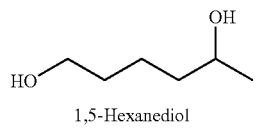
1,5-Hexanediol
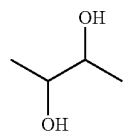
2,3-Butanediol
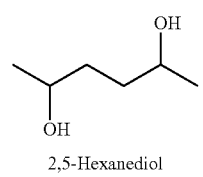
2,5-Hexanediol
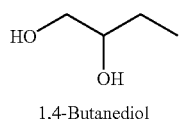
1,4-Butanediol
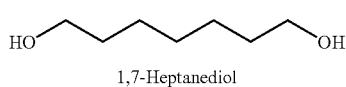
1,7-Heptanediol
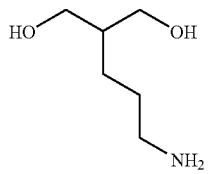
2-(1-Aminopropyl)-1,3-propanediol
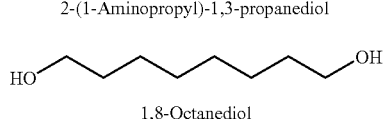
1,8-Octanediol
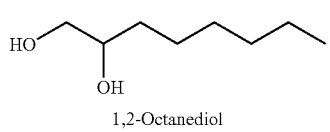
1,2-Octanediol
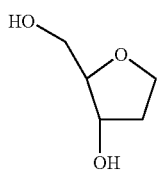
1,2-Dideoxyribose
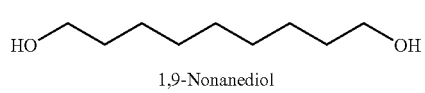 [SMILES: OCCCCCCCCCO]
1,9-Nonanediol
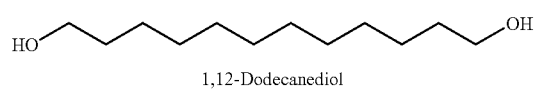 [SMILES: OCCCCCCCCCCCCO]
1,12-Dodecanediol TABLE 2-continued
Representative Non-nucleotidic Linkers
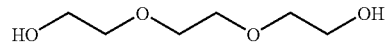
Triethylene glycol
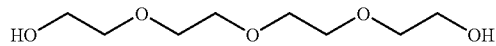
Tetraethylene glycol
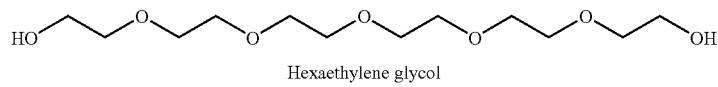 [SMILES: OCCOCCOCCOCCOCCOCCO]
Hexaethylene glycol
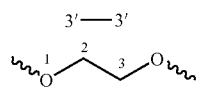
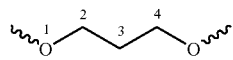
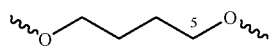
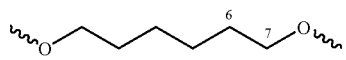
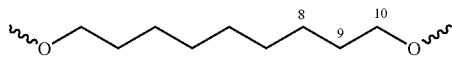
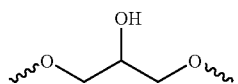
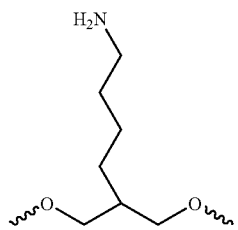
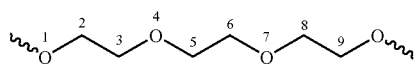
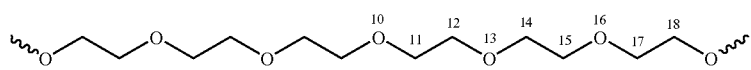
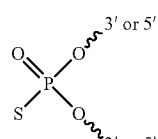
No linker

TABLE 2-continued

Representative Non-nucleotidic Linkers

S, Glycerol brancher
Short linker

B, Sym brancher
Long linker

In some embodiments, the small molecule linker is glycerol or a glycerol homolog of the formula HO—$(CH_2)_o$—CH(OH)—$(CH_2)_p$—OH, wherein o and p independently are integers from 1 to about 6, from 1 to about 4, or from 1 to about 3. In some other embodiments, the small molecule linker is a derivative of 1,3-diamino-2-hydroxypropane. Some such derivatives have the formula HO—$(CH_2)_m$—C(O)NH—$CH_2$—CH(OH)—$CH_2$—NHC(O)—$(CH_2)_m$—OH, wherein m is an integer from 0 to about 10, from 0 to about 6, from 2 to about 6, or from 2 to about 4.

Some non-nucleotidic linkers according to the invention permit attachment of more than two oligonucleotides, as depicted in Table 1. For example, the small molecule linker glycerol has three hydroxyl groups to which oligonucleotides may be covalently attached. Some immune modulatory oligonucleotides according to the invention, therefore, comprise more than two oligonucleotides linked via a non-nucleotidic linker.

In a further embodiment of this aspect of the invention, a TLR9 antagonist compound may contain three or more oligonucleotides linked at their 3' or 5' ends, or through an internucleoside linkage or a functionalized nucleobase or sugar to two or more linkers, as depicted in Table 1. The oligonucleotides of this aspect of the invention may have the same or different sequences. The linkers of this aspect of the invention may be the same or different.

The sequences of specific immune regulatory phosphorothioate oligonucleotide compounds that were used to demonstrate the properties of the compounds encompassed by the invention include those shown in Table 3.

TABLE 3

| Immune Regulatory Oligonucleotide/ SEQ ID NO: | Sequence |
| --- | --- |
| 1 | 5'-TCT<u>GA</u>CGTTTTTTGACGTTCT-3' |
| 2 | 5'-TCTGACGTTTTTT<u>GA</u>CGTTCT-3' |
| 3 | 5'-TCTGACGTTTTTTGACGTTCT-3' |
| 4 | 5'-TCT<u>GA</u>CGTTTTTT<u>GA</u>CGTTCT-3' |
| 5 | 5'-TCT<u>GA</u>CG$_1$TTTTTTGACG$_1$TTCT-3' |
| 6 | 5'-TCTGACG$_1$TTTTTT<u>GA</u>CG$_1$TTCT-3' |
| 7 | 5'-TCTGACG$_1$TTTTTTGACG$_1$TTCT-3' |
| 8 | 5'-TCT<u>GA</u>CG$_1$TTTTTT<u>GA</u>CG$_1$TTCT-3' |
| 9 (control TLR9 agonist) | 5'-CTATCTGACGTTCTCTGT-3' |
| 10 (control TLR9 agonist) | 5'-TCTGACG$_1$TTCT-X-TCTTG$_1$CAGTCT-5' |
| 11 (control non-immune stimulatory oligonucleotide) | 5'-ACACACCAACT-X-TCAACCACACA-5' |
| 12 | 5'-TCT<u>GA</u>CGTTTTTTGACGTTCT-X-TCTTGCAGTTTTTTGC<u>AG</u>TCT-5' |
| 13 | 5'-TCT<u>GA</u>CGTTTTTT<u>GA</u>CGTTCT-X-TCTTGC<u>AG</u>TTTTTTGC<u>AG</u>TCT-5' |

TABLE 3-continued

| Immune Regulatory Oligonucleotide/ SEQ ID NO: | Sequence |
|---|---|
| 14 | 5'-TCT<u>GA</u>CG$_1$TTTTTTGACG$_1$TTCT-X-TCTTG$_1$CAGTTTTTG$_1$C<u>AG</u>TCT-5' |
| 15 | 5'-TCT<u>GA</u>CG$_1$TTTTTT<u>GA</u>CG$_1$TTCT-X-TCTTG$_1$C<u>AG</u>TTTTTG$_1$C<u>AG</u>TCT-5' |

Underlined nucleosides represent 2'-O-methylribonucleosides; G$_1$ = 2'-deoxy-7-deazaguanosine; X = non-nucleotidic linker, for example glycerol.

Figure 2:
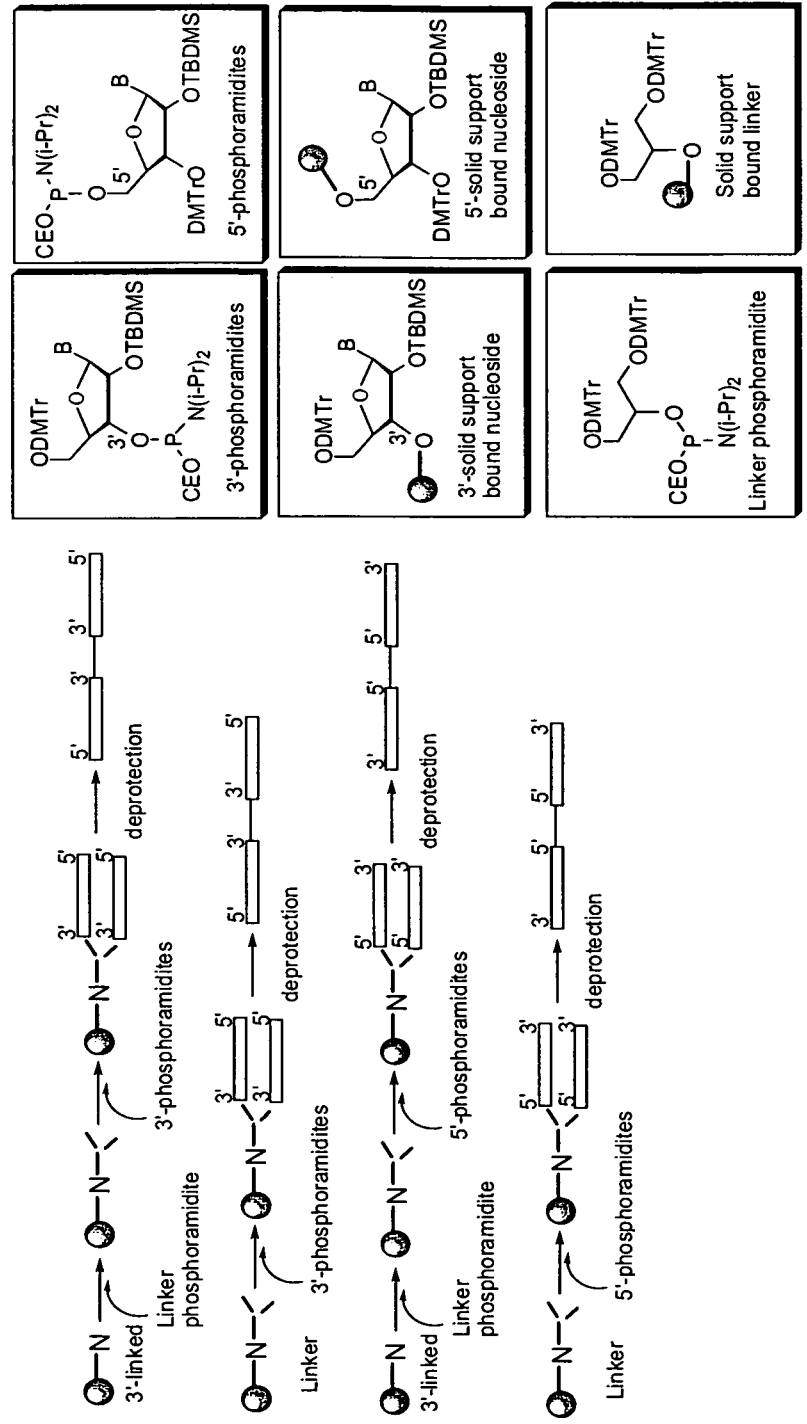
FIG. 2 is a synthetic scheme for the parallel synthesis of compounds of the invention. DMTr=4,4'-dimethoxytrityl; CE=cyanoethyl.

The TLR9 antagonist compounds of the invention may conveniently be synthesized using an automated synthesizer and phosphoramidite approach as schematically depicted in FIGS. 1 and 2, and further described in the Examples. In some embodiments, the immune modulatory oligonucleotides are synthesized by a linear synthesis approach (FIG. 1).

An alternative mode of synthesis is "parallel synthesis", in which synthesis proceeds outward from a central linker moiety (see FIG. 2). A solid support attached linker can be used for parallel synthesis, as is described in U.S. Pat. No. 5,912,332. Alternatively, a universal solid support (such as phosphate attached controlled pore glass) support can be used.

Parallel synthesis of compounds according to the invention has several advantages over linear synthesis: (1) parallel synthesis permits the incorporation of identical monomeric units; (2) unlike in linear synthesis, both (or all) the monomeric units are synthesized at the same time, thereby the number of synthetic steps and the time required for the synthesis is the same as that of a monomeric unit; and (3) the reduction in synthetic steps improves purity and yield of the final immune modulatory oligonucleotide product.

At the end of the synthesis by either linear synthesis or parallel synthesis protocols, the immune modulatory oligonucleotides may conveniently be deprotected with concentrated ammonia solution or as recommended by the phosphoramidite supplier, if a modified nucleoside is incorporated. The product immune modulatory oligonucleotide is preferably purified by reversed phase HPLC, detritylated, desalted and dialyzed.

In a second aspect, the invention provides pharmaceutical formulations comprising a TLR9 antagonist compound according to the invention and a physiologically acceptable carrier.

In a third aspect the invention provides a method for reducing a TLR9-mediated immune response in a mammal, the method comprising administering to the mammal a compound or pharmaceutical formulation according to the invention in an amount that reduces the TLR9-mediated immune response.

In a fourth aspect the invention provides a method for therapeutically treating a mammal having a disease or disorder where reducing a TLR9-mediated immune response would be beneficial, for example, autoimmune disorders, airway inflammation, inflammatory disorders, allergy, asthma, arthritis, arthritis, malaria, allergy, transplant rejection, infectious disease, and other diseases and disorders that have an autoimmune component. The method according to this aspect of the invention comprises administering to the mammal having such a disorder or disease a compound or pharmaceutical formulation according to the invention in a pharmaceutically effective amount.

In a fifth aspect the invention provides a method for preventing a disease or disorder in a mammal where reducing a TLR9-mediated immune response would be beneficial, for example an autoimmune disorder, cancer, airway inflammation, inflammatory disorders, infectious disease, malaria, Lyme disease, ocular infections, skin disorders, psoriasis, scleroderma, cardiovascular disease, atherosclerosis, chronic fatigue syndrome, sarcoidosis, allergy, asthma or a disease caused by a pathogen. The method according to this aspect of the invention comprises administering to a mammal that is susceptible to such a disorder or disease a compound or pharmaceutical formulation according to the invention in a pharmaceutically effective amount.

In some embodiments, the autoimmune disorder is selected from lupus erythematosus, multiple sclerosis, type I diabetes mellitus, irritable bowel syndrome, Chron's disease, rheumatoid arthritis, septic shock, alopecia universalis, acute disseminated encephalomyelitis, Addison's disease, ankylosing spondylitis, antiphospholipid antibody syndrome, autoimmune hemolytic anemia, autoimmune hepatitis, Bullous pemphigoid, chagas disease, chronic obstructive pulmonary disease, coeliac disease, dermatomyositis, endometriosis, Goodpasture's syndrome, Graves' disease, Guillain-Barré syndrome, Hashimoto's disease, hidradenitis suppurativa, idiopathic thrombocytopenic purpura, interstitial cystitis, morphea, myasthenia gravis, narcolepsy, neuromyotonia, pemphigus, pernicious anaemia, polymyositis, primary biliary cirrhosis, schizophrenia, Sjögren's syndrome, temporal arteritis ("giant cell arteritis"), vasculitis, vitiligo, vulvodynia and Wegener's granulomatosis.

In some embodiments, the inflammatory disorder is selected from airway inflammation, asthma, autoimmune diseases, chronic inflammation, chronic prostatitis, glomerulonephritis, Behçet's disease, hypersensitivities, inflammatory bowel disease, reperfusion injury, rheumatoid arthritis, transplant rejection, ulcerative colitis, uveitis, conjunctivitis and vasculitis.

In any of the methods according to the invention, the TLR9 antagonist compound can variously act by producing direct TLR9 antagonist effects alone and/or in combination with any other agent useful for treating or preventing the disease or condition that does not diminish the TLR9 antagonist effect of the compound. In any of the methods according to the invention, the agent(s) useful for treating or preventing the disease or condition includes, but is not limited to, vaccines, antigens, antibodies, preferably monoclonal antibodies, cytotoxic agents, allergens, antibiotics, siRNA, antisense oligonucleotides, other TLR agonist or antagonist (e.g. agonists or antagonist of TLR7, TLR8 and/or TLR3), chemotherapeutic agents (both traditional chemotherapy and modern targeted therapies), targeted therapeutic agents, activated cells, peptides, proteins, gene therapy vectors, peptide vaccines, protein vaccines, DNA vaccines, adjuvants, and co-stimulatory molecules (e.g. cytokines, chemokines, protein ligands, trans-activating factors, peptides or peptides comprising modified amino acids), or combinations thereof. Alternatively, the agent can include DNA vectors encoding for antigen or allergen. Alternatively, the compounds can be administered in combination with other adjuvants to enhance the specificity or magnitude of the immune response to the compound.

In any of the methods according to the invention, administration of TLR9 antagonist compound, alone or in combination with any other agent, can be by any suitable route, including, without limitation, parenteral, mucosal delivery, oral, sublingual, transdermal, topical, inhalation, intranasal, aerosol, intraocular, intratracheal, intrarectal, vaginal, by gene gun, dermal patch or in eye drop or mouthwash form. Administration of the therapeutic compositions of TLR9 antagonist compound can be carried out using known procedures using an effective amount and for periods of time effective to reduce symptoms or surrogate markers of the disease. For example, an effective amount of a TLR9 antagonist compound for treating a disease and/or disorder could be that amount necessary to alleviate or reduce the symptoms, or delay or ameliorate an autoimmune response. The effective amount for any particular application can vary depending on such factors as the disease or condition being treated, the particular oligonucleotide being administered, the size of the subject, or the severity of the disease or condition. One of ordinary skill in the art can empirically determine the effective amount of a particular oligonucleotide without necessitating undue experimentation.

When administered systemically, the therapeutic composition is preferably administered at a sufficient dosage to attain a blood level of TLR9 antagonist compound from about 0.0001 micromolar to about 10 micromolar. For localized administration, much lower concentrations than this may be effective, and much higher concentrations may be tolerated. Preferably, a total dosage of TLR9 antagonist compound ranges from about 0.001 mg per patient per day to about 200 mg per kg body weight per day. It may be desirable to administer simultaneously, or sequentially a therapeutically effective amount of one or more of the therapeutic compositions of the invention to an individual as a single treatment episode.

The TLR9 antagonist compound may optionally be linked to one or more allergens and/or antigens (self or foreign), an immunogenic protein, such as keyhole limpet hemocyanin (KLH), cholera toxin B subunit, or any other immunogenic carrier protein. TLR9 antagonist compounds can also be used in combination with other compounds (e.g. adjuvants) including, without limitation, Freund's incomplete adjuvant, KLH, monophosphoryl lipid A (MPL), alum, and saponins, including QS-21 and imiquimod, or combinations thereof.

The methods according to this aspect of the invention are useful for model studies of the immune system. The methods are also useful for the prophylactic or therapeutic treatment of human or animal disease. For example, the methods are useful for pediatric and veterinary vaccine applications.

The examples below are intended to further illustrate certain preferred embodiments of the invention, and are not intended to limit the scope of the invention.

EXAMPLES

Example 1

TLR9 Antagonist Compounds Synthesis

The immune modulatory oligonucleotides were chemically synthesized using phosphoramidite chemistry on automated DNA/RNA synthesizer. TAC protected (Except U) 2'-O-TBDMS RNA monomers, A, G, C and U, were purchased from Sigma-Aldrich. 7-deaza-G, inosine and loxoribine monomers were purchased from ChemGenes Corporation. 0.25M 5-ethylthio-1H-tetrazole, PAC-anhydride Cap A and Cap B were purchased from Glen Research. 3% trichloroacetic acid (TCA) in dichloromethane (DCM) and 5% 3H-1,2-Benzodithiole-3-one-1,1-dioxide (Beaucage reagent) were made in house.

TLR9 antagonist compounds were synthesized at 1-2 μM scale using a standard DNA synthesis protocol.

Cleavage and Base Deprotection

TLR9 antagonist compounds were cleaved from solid support and the solution was further heated at 65° C. to removing protecting groups of exo cyclic-amines. The resulting solution was dried completely in a SpeedVac.

Ion Exchange HPLC Purification

TLR9 antagonist compounds were purified by ion exchange HPLC.

Column: Dionex DNAPac 100 column (22×250)

Column Heater ChromTech TL-105 HPLC column heater, temperature is set to 80° C.

Buffer A: 20 mM Tris-HCl, pH 7.0, 20% acetinitrile

Buffer B: 3.0 M NaCl, 20 mM Tris-HCl, pH 7.0, 20% acetonitrile

Flow rate: 10 ml/min

Gradient:
    0-2 min: 0% B
    2-11 min: 0% B to 35% B
    11-41 min: 35% B to 90% B
    41-45 min: 100% B Crude TLR9 antagonist compounds solution was injected into HPLC. Above gradient is performed and the fractions were collected. All fractions containing more than 90% desired product were mixed, and then the solution was concentrated to almost dry by RotoVap. Distilled deionized water was added to make final volume of 10 ml.

C-18 Reversed Phase Desalting tC-18 Sep-Pak cartridge purchased from Waters was first conditioned with 10 ml of acetonitrile followed by 10 ml of 0.5 M sodium acetate. 10 ml of immune modulatory oligonucleotide solution was loaded. 15 ml of water was then used to wash out the salt. The immune modulatory oligonucleotide was finally eluted out by 1 ml of 50% acetonitrile in water.

The solution is placed in SpeedVac for 30 minutes. The remaining solution was filtered through a 0.2 micro filter and then was lyophilized to dryness. The solid was then re-dissolved in water to make the desired concentration.

The final solution was stored below 0° C.

Capillary Electrophoresis

Following synthesis and purification, the TLR9 antagonist compounds were analyzed by capillary electrophoresis.

Instrument: Beckman 5010
    Capillary: 62 cm ssDNA capillary
    Sample preparation: 0.2 OD of TLR9 antagonist compounds was dissolved in 200 ul of distilled deionized water.
    Injection: electro-kinetic injection at 5 KV for 5 seconds.
    Running condition: 14 KV for 50 minutes at 30° C.

Ion Exchange HPLC Analysis

Following synthesis and purification, the TLR9 antagonist compounds were analyzed by ion exchange HPLC.

Column: Dionex DNAPac guard column (22×250)

Column Heater ChromTech TL-105 HPLC column heater, temperature is set to 80° C.

Buffer A: 100 mM Tris-HCl, pH 8.0, 20% acetinitrile

Buffer B: 2.0 M LiCl, 100 mM Tris-HCl, pH 8.0, 20% acetonitrile

Flow rate: 2 ml/min

Gradient:
    0-2 min: 0% B
    2-10 min: 0% B to 100% B
    10-15 min: 100% B

PAGE Analysis 0.3 OD of immune modulatory oligonucleotide was loaded on 20% polyacrylamide gel and was electrophoresed at constant power of 4 watts for approximately 5 hours. The gel was viewed under short wavelength UV light.

Example 2

Human Cell Culture Protocols

HEK293/human TLR7 or HEK293/human TLR8 cells (In-vivogen, San Diego, Calif.) were cultured in 48-well plates in 250 µl/well DMEM supplemented with 10% heat-inactivated FBS in a 5% $CO_2$ incubator.

Reporter Gene Transformation

HEK293 cells stably expressing mouse TLR9 (Invivogen, San Diego, Calif.) were cultured in 48-well plates in 250 µl/well DMEM supplemented with 10% heat-inactivated FBS in a 5% $CO_2$ incubator. At 80% confluence, cultures were transiently transfected with 400 ng/ml of SEAP (secreted form of human embryonic alkaline phosphatase) reporter plasmid (pNifty2-Seap) (Invivogen) in the presence of 4 µl/ml of lipofectamine (Invitrogen, Carlsbad, Calif.) in culture medium. Plasmid DNA and lipofectamine were diluted separately in serum-free medium and incubated at room temperature for 5 minutes. After incubation, the diluted DNA and lipofectamine were mixed and the mixtures were incubated at room temperature for 20 minutes. Aliquots of 25 µl of the DNA/lipofectamine mixture containing 100 ng of plasmid DNA and 1 µl of lipofectamine were added to each well of the cell culture plate, and the cultures were continued for 4 hours.

TLR9 Antagonist Treatment

After transfection, medium was replaced with fresh culture medium, TLR9 antagonist compounds were added to the cultures, and the cultures were continued for 18 hours. At the end of treatment, 30 µl of culture supernatant was taken from each treatment and used for SEAP assay following manufacturer's protocol (Invivogen).

SEAP Assay

Figure 3:
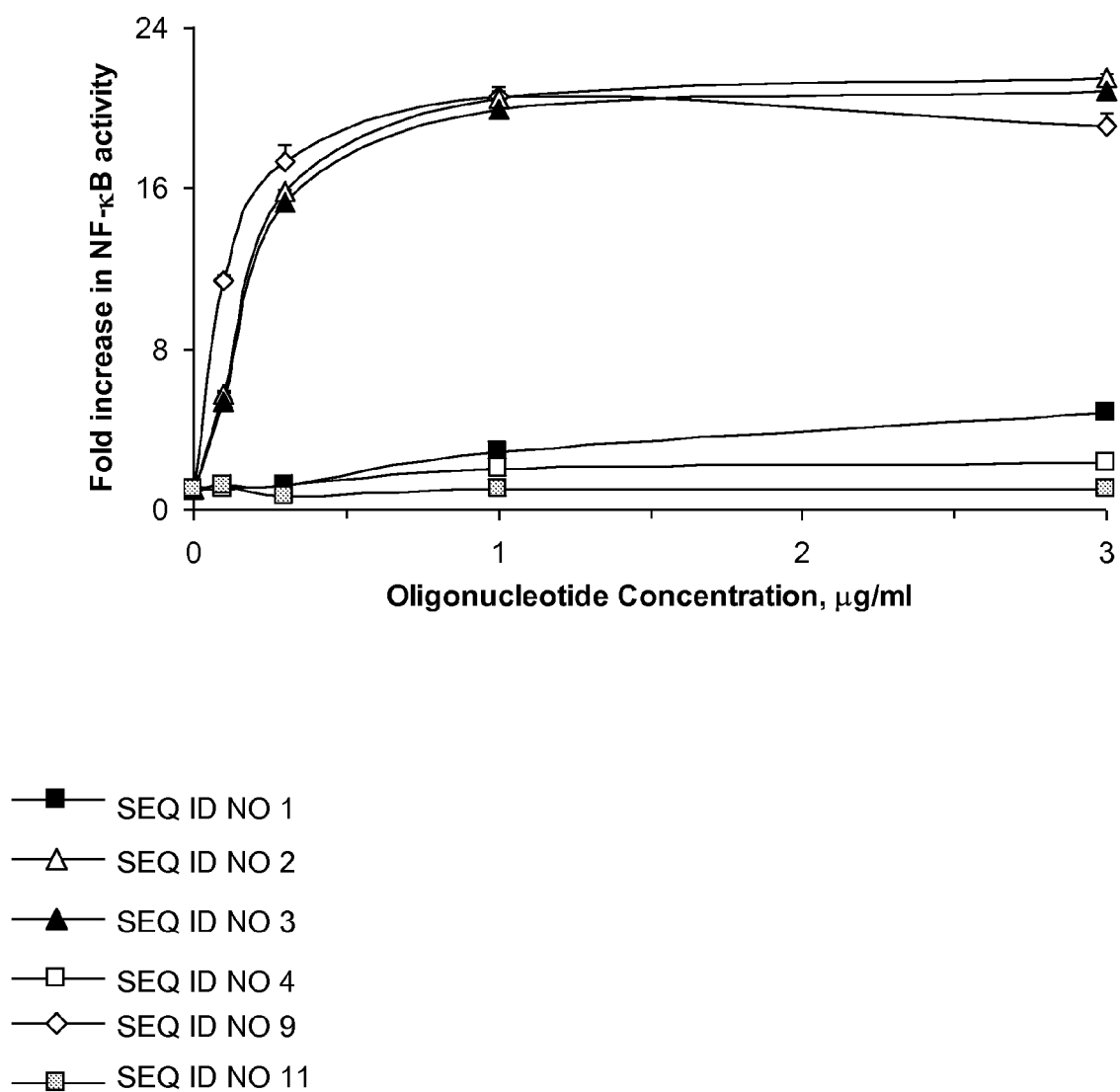
FIG. 3 depicts TLR9 activity mediated by the novel immune regulatory oligonucleotides.

Briefly, culture supernatants were incubated with p-nitrophynyl phosphate substrate and the yellow color generated was measured by a plate reader at 405 nm. The data are shown as fold increase in NF-κB activity over PBS control. (Putta M R et al, Nucleic Acids Res, 2006, 34:3231-8). The results are shown in FIG. 3.

Example 3

Figure 4:
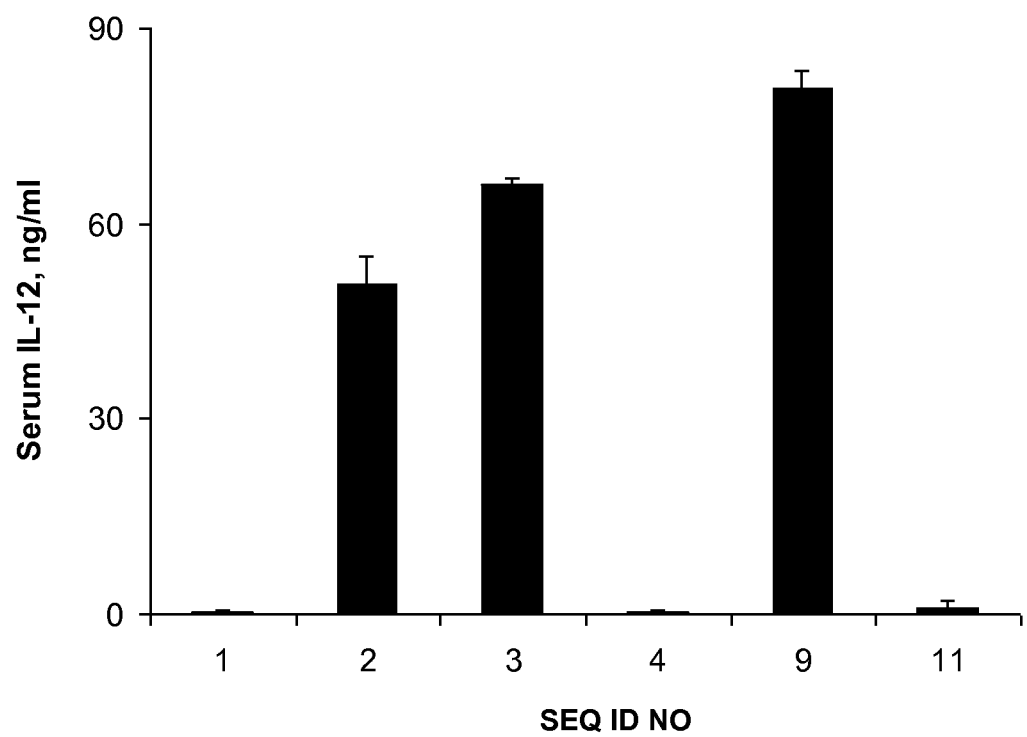
FIG. 4 depicts TLR9 activity mediated by the novel immune regulatory oligonucleotides at lower doses.
Figure 5:
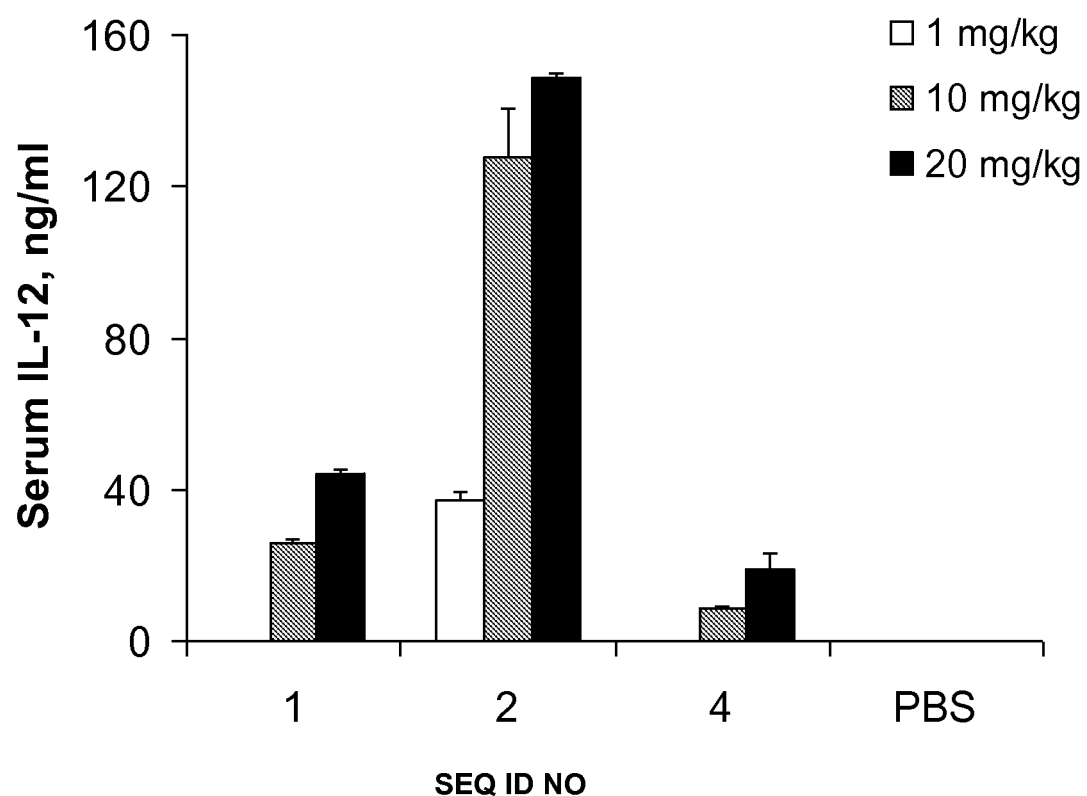
FIG. 5 depicts TLR9 activity of the novel immune regulatory oligonucleotides at increasing doses.
Figure 6:
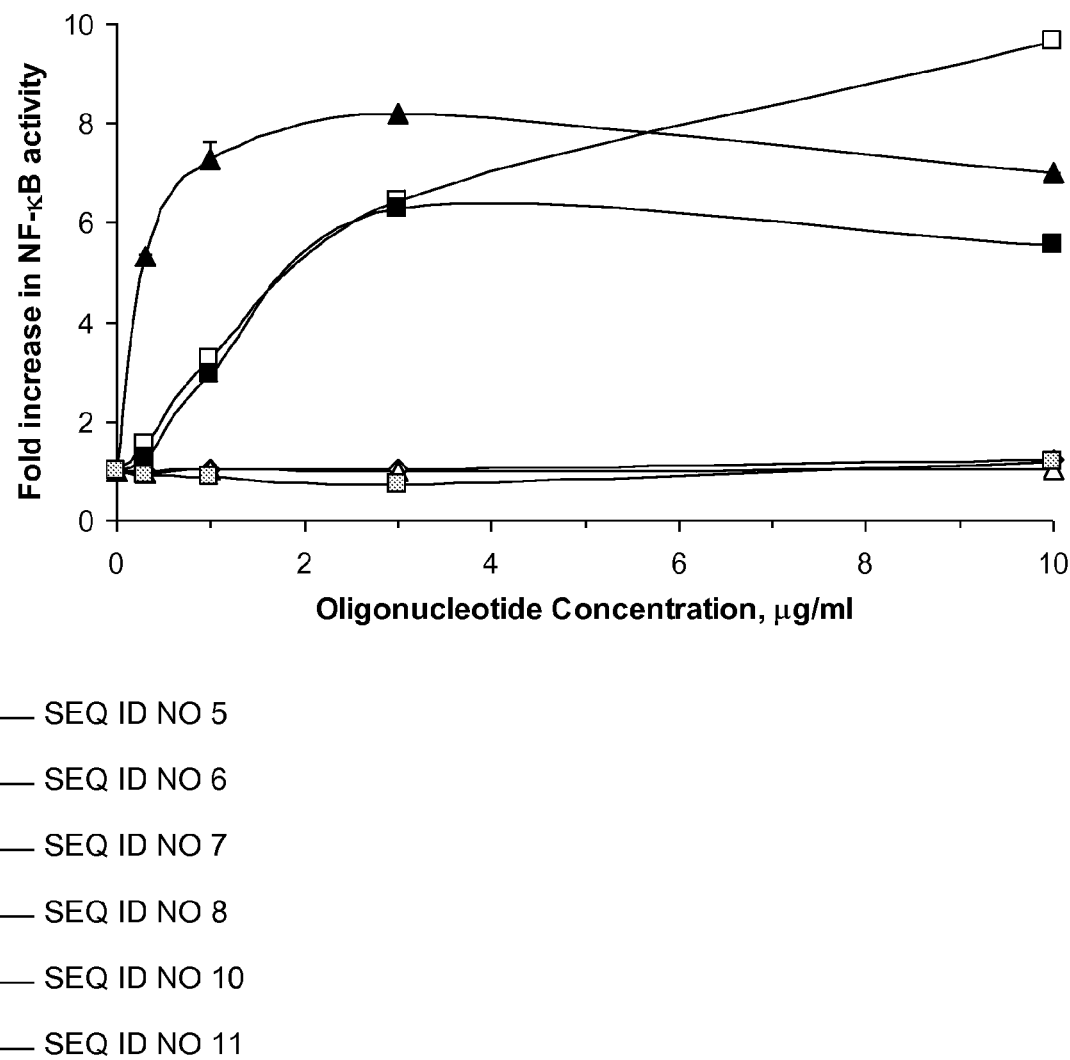
FIG. 6 depicts TLR9 activity of the novel immune regulatory oligonucleotides.
Figure 7:
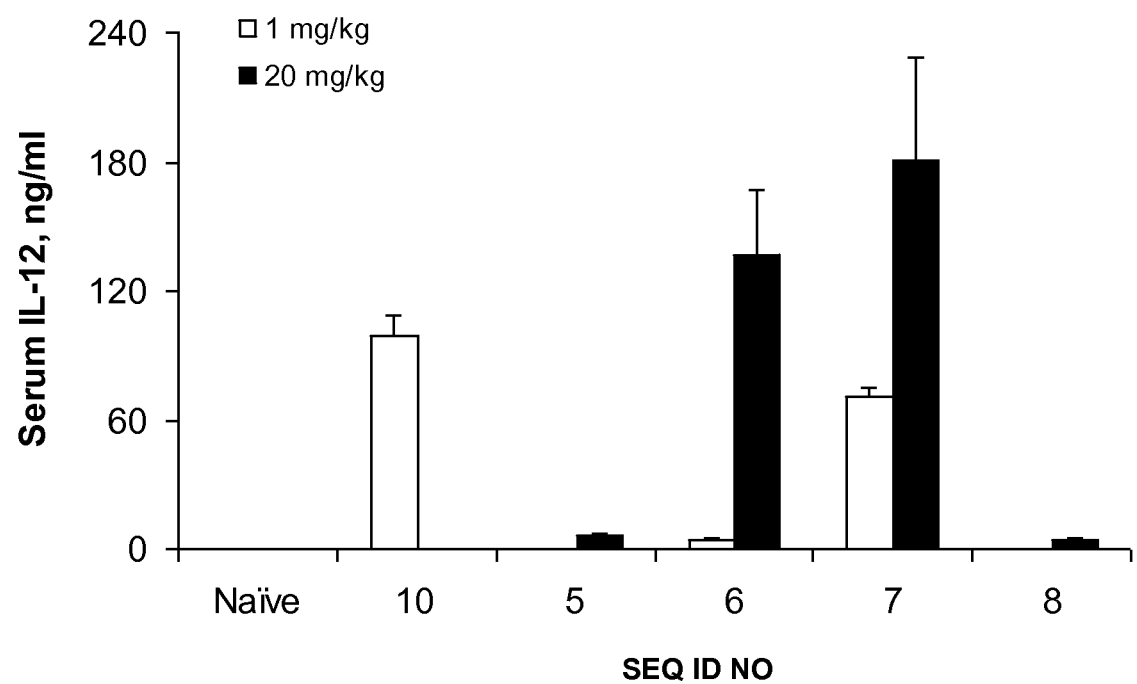
FIG. 7 depicts TLR9 activity of the novel immune regulatory oligonucleotides at increasing doses.

In Vivo IL-12 Secretion in Mouse Model Treated with Dosage Controlled TLR9 Antagonist Compounds C57BL/6 mice and BALB/c mice, 6-8 weeks old, were obtained from Taconic Farms, Germantown, N.Y. and maintained in accordance with Idera Pharmaceutical's IACUC approved animal protocols. Mice (n=3) were injected subcutaneously (s.c) with individual immune regulatory oligonucleotides from Table 3 at 1, 10, or 20 mg/kg (single dose). Serum was collected 2 hr after immune modulatory oligonucleotide administration and cytokine and chemokine concentrations were determined by sandwich ELISA or Luminex multiplex assays. The results are shown for IL-12 in FIGS. 4, 5, and 7 and demonstrate that in vivo administration of immune regulatory oligonucleotides containing novel chemical compositions generates unique cytokine profiles. All reagents, including cytokine and chemokine antibodies and standards were purchased from PharMingen. (San Diego, Calif.).

EQUIVALENTS

While the foregoing invention has been described in some detail for purposes of clarity and understanding, it will be appreciated by one skilled in the art from a reading of this disclosure that various changes in form and detail can be made without departing from the true scope of the invention and appended claims.

---

What is claimed is:

1. A compound that acts as a TLR9 antagonist at a first dosage and acts as a TLR9 agonist at a second, higher dosage wherein the compound comprises at least two oligonucleotides linked via a direct nucleotide to nucleotide linkage at their 3' ends through the 3' positions of the sugars or through a modified sugar or modified nucleobase or via a non-nucleotide linker at their 3' ends through the 3' positions of the sugars or through a modified sugar or modified nucleobase; wherein at least one of the two oligonucleotides has the structure 5'-$N_m$—$N_1N_2C_1G_1$-$N_p$—$N_3N_4C_2G_2$-$N_m$-3', wherein $C_1$ and $C_2$ are independently cytosine, 2'-deoxycytidine, or a cytosine derivative selected from the group consisting of arabinocytidine, 2'-deoxy-2'-substituted-arabinocytidine, 2'-O-substituted-arabinocytidine, 2'-deoxy-5-hydroxycytidine, 2'-deoxy-N4-alkyl-cytidine, 2'-deoxy-4-thiouridine and other non-natural pyrimidine nucleosides, and $G_1$ and $G_2$ are independently guanosine, 2'-deoxyguanosine or a guanosine derivative selected from the group consisting of 2'-deoxy-7-deazaguanosine, 2'-deoxy-6-thioguanosine, arabinoguanosine, 2'-deoxy-2'substituted-arabinoguanosine, 2'-O-substituted-arabinoguanosine, 2'-deoxyinosine, and other non-natural purine nucleosides, wherein at least one of $C_1$ and $G_1$ is a derivative nucleoside; $N_2$ is a blocking moiety that inhibits the TLR stimulatory activity of $C_1G_1$ selected from the group consisting of 2'-substituted nucleotide, 3'-OMe-ribonucleoside, 3-nitropyrrole, 5-nitroindole, dU, β-L-deoxynucleoside, α-deoxynucleoside, and abasic nucleoside;

$N_1$ is a i) nucleotide;

ii) nucleotide derivative selected from the group consisting of 7-deaza-G, ara-G, 6-thio-G, Inosine, Iso-G, loxoribine, TOG(7-thio-8-oxo)-G, 8-bromo-G, 8-hydroxy-G, 5-aminoformycin B, Oxoformycin, 7-methyl-G, 9-p-chlorophenyl-8-aza-G, 9-phenyl-G, 9-hexyl-guanine, 7-deaza-9-benzyl-G, 6-Chloro-7-deazaguanine, 6-methoxy-7-deazaguanine, 8-Aza-7-deaza-G(PPG), 2-(Dimethylamino)guanosine, 7-Methyl-6-thioguanosine, 8-Benzyloxyguanosine, 9-Deazaguanosine, 1-(B-D-furanosyl)-2-oxo-7-deaza-8-methyl-purine, 9-benzyl-8-hydroxy-2-(2-methoxyethoxy)adenine, 2-Amino-N2-O—, methyladenosine, 8-Aza-7-deaza-A, 7-deaza-A, Vidarabine, 2-Aminoadenosine, N1-Methyladenosine, 8-Azaadenosine, 5-Iodotubercidin, 2'-deoxy-5-hydroxycytidine, 2'-deoxy-N4-alkyl-cytidine and 4-thio-U or iii) blocking moiety that inhibits the TLR stimulatory activity of $C_1G_1$ selected from the group consisting of 2'-substituted nucleotide, 3'-OMe-ribonucleoside, 3-nitropyrrole, 5-nitroindole, dU, β-L-deoxynucleoside, α-deoxynucleoside and abasic nucleoside;

$N_3$ and $N_4$, at each occurrence, is independently a nucleotide or nucleotide derivative that does not inhibit the TLR stimulatory activity of $C_2G_2$;

$N_m$, at each occurrence, is independently a nucleotide, nucleotide derivative or non-nucleotide linkage;

$N_p$, at each occurrence, is independently a nucleotide or nucleotide derivative, provided that the compound contains less than 3 consecutive guanosine nucleotides, wherein m is a number from 0 to about 20, wherein p is a number from 0 to about 20.

2. The compound according to claim 1, wherein the non-nucleotidic linker is an alkyl linker or amino linker, wherein the alkyl or amino linker may be optionally branched or unbranched, cyclic or acyclic, substituted or unsubstituted, saturated or unsaturated, chiral, achiral or racemic mixture.

3. The compound according to claim 2, wherein the alkyl linker has from about 2 to about 18 carbon atoms.

4. The compound according to claim 2, wherein the alkyl linker has from about 3 to about 9 carbon atoms.

5. The compound according to claim 2, wherein the alkyl linker is selected from 1,2,3-Propanetriol, 1,2,4-Butanetriol, 2-Hydroxymethyl-1,3-proanediol, 1,1,1-Tris(hydroxymethyl)ethane, 2-Amino-2-(hydroxymethyl)1,3-proanediol, tris(hydroxymethyl)nitromethane, 1,1,1-Tri(hydroxymethyl)propane, 1,2,6-Hexanetriol, 1,3,5-Hexanetriol, 1,3,5-Pentanetriol, 3-Methyl-1,3,5-pentanetriol, 1,2,3-Heptanetriol, 2-(Hydroxymethyl)1,4-butanediol, 1,3-Di(hydroxymethyl)phenol, 1,3,5-Tri(hydroxymethyl)benzene, 1,3-Di(hydroxyethoxy)-2-hydroxy-propane, 1,3-Di(hydroxypropoxy)-2-hydroxy-propane, D-Galactal, 1,3,5-Tris(2-hydroxyethyl)cyanuric acid, 1,3,5-Tris(4-hydroxyphenyl)benzene, 1,3-Propanediol, 1,2-Propanediol, 1,4-Butanediol, 1,3-Butanediol, 2,3-Butanediol, 1,4-Butanediol, 1,5-Pentanediol, 2,4-Pentanediol, 1,6-Hexanediol, 1,2-Hexanediol, 1,5-Hexanediol, 2,5-Hexanediol, 1,7-Heptanediol, 1,8-Octanediol, 1,2-Octanediol, 1,9-Nonanediol, 1,12-Dodecanediol or 2-(1-Aminopropyl)-1,3-propanediol.

6. A pharmaceutical composition comprising a compound according to any one of claims 1 and 2-5 and a pharmaceutically acceptable carrier.

7. The compound according to claim 1, wherein the blocking moiety is a 2'-substituted nucleotide selected from the group consisting of a nucleotide or arabinotide substituted with a saturated or unsaturated ($C_1$-$C_6$) hydrocarbyl group, halogen atom, 2'-amino, 2'-fluoro, 2'-allyl, 2'-O-alkyl, 2'-propargyl, 2'-O-methyl, 2'-O-methoxyethoxy and with an aryl group having 6-10 carbon atoms, wherein such hydrocarbyl or aryl group may be unsubstituted or may be substituted with halo, hydroxy, trifluoromethyl, cyano, nitro, acyl, acyloxy, alkoxy, carboxyl, carboalkoxy.

* * * * *